United States Patent [19]

Dale et al.

[11] Patent Number: 4,665,027
[45] Date of Patent: May 12, 1987

[54] IMMOBILIZED CELL REACTOR-SEPARATOR WITH SIMULTANEOUS PRODUCT SEPARATION AND METHODS FOR DESIGN AND USE THEREOF

[75] Inventors: M. Clark Dale; Philip C. Wankat, both of Lafayette; Martin R. Okos, Battleground, all of Ind.

[73] Assignee: Bio-Process Innovation, Inc., West Lafayette, Ind.

[21] Appl. No.: 548,531

[22] Filed: Nov. 3, 1983

[51] Int. Cl.$^4$ .......................... C12P 7/14; C12M 1/40
[52] U.S. Cl. .................................... 435/162; 435/288; 435/813; 435/819
[58] Field of Search ............... 435/288, 161, 162, 310, 435/313, 813, 819, 163; 210/150

[56] References Cited

U.S. PATENT DOCUMENTS

| | | | |
|---|---|---|---|
| 2,053,770 | 9/1936 | Dreyfus | 435/161 |
| 2,146,326 | 2/1939 | Bergius et al. | 435/313 X |
| 3,919,048 | 11/1975 | Dahlmans et al. | 435/177 |
| 4,009,075 | 2/1977 | Hoge | 435/162 |
| 4,033,820 | 7/1977 | Brouillard | 435/288 X |
| 4,251,231 | 2/1981 | Baird . | |
| 4,266,026 | 5/1981 | Breslan | 435/288 X |
| 4,297,172 | 10/1981 | Kyle . | |
| 4,306,884 | 12/1981 | Roth . | |
| 4,327,184 | 4/1982 | Johnson et al. | 435/161 X |
| 4,336,335 | 6/1982 | Muller et al. | 435/162 X |
| 4,337,315 | 6/1982 | Fukushima et al. | 435/813 X |
| 4,350,765 | 9/1982 | Chibata et al. | 435/162 X |
| 4,425,433 | 1/1984 | Neves | 435/813 X |
| 4,510,242 | 4/1985 | Tedder | 435/161 X |

FOREIGN PATENT DOCUMENTS 0006882  1/1984  Japan .................................. 435/161

OTHER PUBLICATIONS

Levenspiel, Chemical Reaction Engineering, N.Y., John Wiley and Sons, 1963, pp. 99-105, 250.
Perry et al., (Ed.) Chemical Engineers Handbook, N.Y., McGraw-Hill, fourth edition, 1963, pp. 18-23.
Andiappan et al, "Prediction of Isobaric Vapor-Liquid Equilibrium Data for Mixtures of Water and Simple Alcohols", Adv. in Chem. Series 115, 6: 93, 1972.
Gencer et al, "Ethanol Fermentation in a Yeast Immobilized Tubular Fermentor", Biotechnology and Bioengineering, vol. 25, 1983, pp. 2243-2262.
Rasquin et al, "Vacuum Degassing of Carbon Dioxide and Oxygen from Water in Packed Columns", Ind. Eng. Chem. Fundam., vol. 16, No. 1, 1977, pp. 103-108.
Tyagi et al, "Studies on Immobilized *Saccharomyces cerevisiae*. I. Analysis of Continuous Rapid Ethanol Fermentation in Immobilized Cell Reactor", Biotechnology and Bioengineering 24, 1982, pp. 781-795.
Ghose, T. K. and Tyagi, R. D., Biotechnology & Bioengineering, vol. XXI, pp. 1387-1400 (1979).
Ghose, T. K. and Bandyopadhyay, K. K., Biotechnology & Bioengineering, vol. XXII, pp. 1489-1496 (1980).

(List continued on next page.)

Primary Examiner—Robert J. Warden
Assistant Examiner—Randall E. Deck
Attorney, Agent, or Firm—Berman, Aisenberg & Platt

[57] ABSTRACT

A novel immobilized cell reactor design is described capable of separating an inhibitory metabolite from a fermentation broth as it is formed. This reactor has the dual advantages of (1) speeding product inhibited reactions and (2) giving a concentrated product free of substrate and cells. The immobilized cell reactor separator (ICRS) can consist of two columns; in the first or 'enriching' column stripping gas and broth move co-currently after which the liquid phase moves to the top of the second 'stripping' column and moves counter currently to the stripping gas while the remaining substrate is converted to product. The use of this reactor in an ethanol from whey lactose fermentation system is also described.

8 Claims, 18 Drawing Figures

OTHER PUBLICATIONS

Ghose, T. K. and Bandyopadhyay, K. K., Biotechnology & Bioengineering, vol. XXIV, pp. 797–804 (1982).

Ladisch, M. R. and Tsao, G. T., J. Chromatography, vol. 166, pp. 85–100 (1978).

Moulin, G., Maguy, G. and Galzy, P., Biotechnology & Bioengineering, vol. XXII, pp. 1277–1281 (1980).

Norton Chemical Process Products; Design Information for Packed Towers; Bulletin DC-11.

Cysewski, G. R. and Wilke, C. R., Biotechnology & Bioengineering, vol. XX, pp. 1421–1444 (1978).

Shah, Y. T., Gas-Liquid-Solid Reactor Design, McGraw Hill (1979) Chapter 1, pp. 1–21.

Dale, M. C., Okos, M. R. and Wankat, P. C., Paper to be presented at AICHE meeting, Nov. 15–20, 1982.

Dale, M. C., Okos, M. R. and Wankat, P. C., Biotechnology & Bioengineering, vol. XXVII, pp. 932–952 (1985).

Aiba, S., M. Shoda, and M. Nagatani, 1968, Kinetics of Product Inhibition in Alcohol Fermentation, Biotech. Bioeng., 10:845.

Bandyopadhyay, K. and T. K. Ghose, 1982, Studies on Imm. S. Cerev.:Phys. of Growth and Metab. on Various Supports, Biotech. Bioeng., 24:805.

Beebe, H., K. E. Coulter, A. Lindsay and E. M. Baker, 1942, Equil. in Ethanol-Water System at Pressures less than Atmospheric, Ind. and Eng. Chem., 34, 12:1501.

Black, C., 1959, Phase Equilibrium in Mixtures of Polar and Non-Polar Compounds, AICHE J., 5(2):249–255.

Black, C. and D. E. Ditsler, 1972, Dehydration of Aqueous Ethanol Mixtures, Adv. in Chem. Series, 64:115.

Cysewski, G. R. and C. R. Wilke, 1977, Rapid Ethanol Fermentation Using Vacuum and Cell Recycle, Biotech. Bioeng., 19:1125.

Dankwerts, P., 1951, Significance of Liquid-Film Coefficients in Gas Absorption, IEC, 43:1460.

Dankwerts, P., 1955, Gas Absorption Accompanied by Chemical Reaction, AICHE J., 1:456.

Deckwer, W., R. Burckhort and G. Zoll, 1974, Mixing and Mass Transfer in Tall Bubble Columns, Chem. Eng. Sci., 29:2177.

Eckert, J., 1979, Design of Packed Columns, from Handbook of Sep. Tech. for Chem. Eng., ed by P. Schweitzer, McGraw-Hill, New York, N.Y.

Gawel, J. and J. Kosikowski, 1978, Improving Alcohol Fermentation in Conc. UF Permeate of Cottage Cheese Whey., J. Food Sci., 43:1717.

Griffith, W. L. and A. L. Compere, 1975, A New Method for Coating Tower Packing so as to Facilitate Microbial Attachment, SIM Annual Report, Chapter 25, 241.

Jelinek, J. and V. Hlavalcek, 1976, Steady State Counter Current Equil. Stage Separation with Chem. Reaction by Relaxation Method, Chem. Eng. Comm., 2:79.

Jelinek, J., V. Hlavalcek and M. Kubicek, 1973, Multi Component, Multi Stage Separation by Relaxation Procedure, Chem. Eng. Sci., 28:1825.

Linek, V., V. Stoy, V. Machon, and Z. Krivski, 1974, Chem. Engr. Sci., 29:1955.

Magnussen P. and V. Schumacher, 1978, Axial Mixing of Liquid in Packed Bubble Columns and Perforated Plates of Large Diameter, Chem. React. Eng. ACS Symp. Series, 65:493.

Minier, M. and G. Goma, 1982, Ethanol Production by Extractive Fermentation, Biotech. Bioengr., 25:1565.

Moulin, G., H. Bose, and P. Galzy, 1980, Inhib. of Alcoholic Ferm. by Substrate and Ethanol, Biotech. Bioeng., 22:2375.

Nelson, P. A., 1971, Countercurrent Equilibrium Stage Operation with Reaction, AICHE J., 17,5:1043.

Norton Co., 1975, Data and Specifications for Intalox Saddles, Company Literature.

Ohki, Y. and H. Inoue, 1970, Longitudinal Mixing of Liquid Phase in Bubble Columns, Chem. Engr. Sci., 25:1.

Ramalingham, A., and R. K. Finn, 1977, The Vacuferm Process: A New Approach to Fermentation Alcohol, Biotech. Bioeng., 19:583.

Rittman, B., 1982, Effect of Shear Stress on Biofilm Loss Rate, Biotech. Bioeng., 24:501.

Rittman, B. and P. McCarty, 1980, Steady State Biofilm Analysis, Biotech. Bioeng., 22:2243.

Sitton, O. C. and J. L. Gaddy, 1980, Ethanol Production in an Immobilized Cell Reactor, Biotech. Bioeng., 22:1735.

Spear, M., 1981, Low Energy Route to Ethanol from Biomass, P.E., 2:85.

OTHER PUBLICATIONS

Tierney, J. W. and J. A. Bruno, 1967, Equil. Stage Calculations, AICHE J., 13, 3:556.

Dean, R. C., Jr. and Venkata Subramanian, K.; Continuous Fermentation with Fluidized Slurries of Immobilized Microorganisms, Paper No. 37, Microbial and Biochemical Technology Division, ACS, Aug. 30, 1983.

Falch, E. A. and Gaden, E. L., Jr., A Continuous Multistage Tower Fermentor., Biotech. & Bioeng., vol. XI, pp. 927-943 (1969).

Hong, J., Voloch, M., Ladisch, M. R. and Tsao, G. T., Absorption of Ethanol-Water Mixtures by Biomass Materials, Biotech. & Bioeng., vol. XXIV, pp. 725-730 (1982).

Hsu, K. H., Erickson, L. E. and Fan, L. T.; Pressure Drop, Gas Hold-Up, and Oxygen Transfer in Tower Systems, Biotech. and Bioeng., vol. XIX, pp. 247-265 (1977).

Leao, C. and Van Uden, N., Effects of Ethanol and Other Alkanols on the Kinetics and the Activation Parameters of Thermal Death in *Saccharomyces cerevisiae*, Biotech. & Bioeng., vol. XXIV, pp. 1581-1590 (1982).

Alcoholic Fermentation in an Aqueous Two-Phase System, Biotech. & Bioeng., vol. XXII, pp. 2393-2398 (1980).

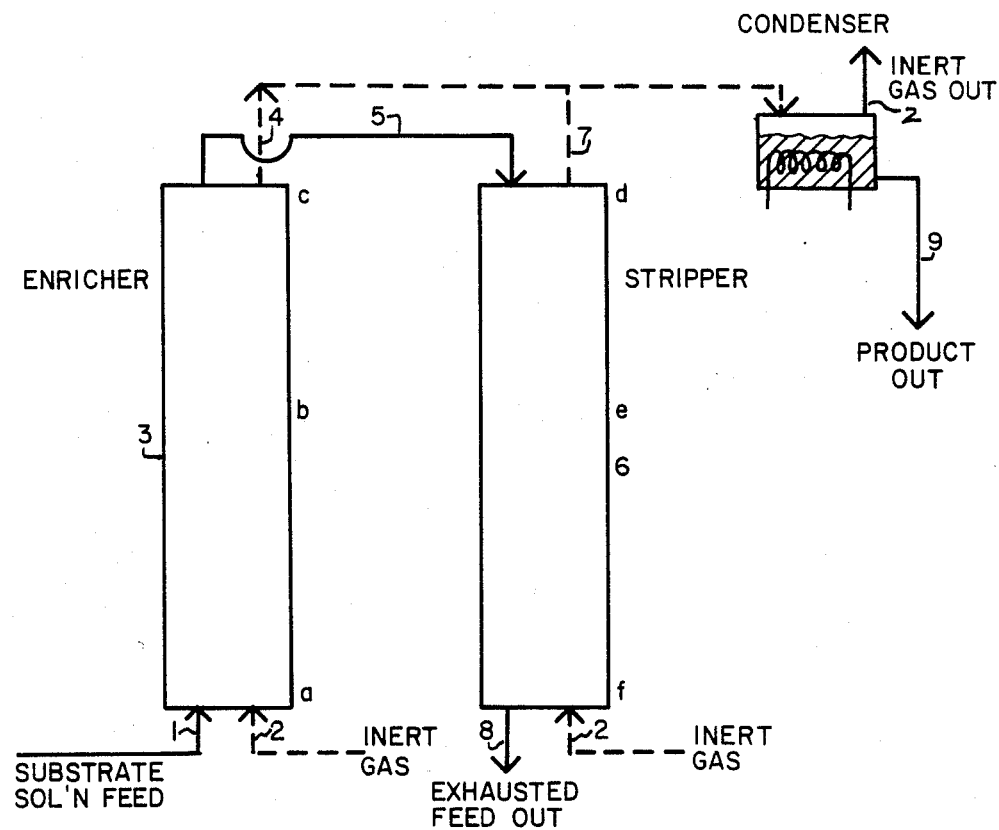
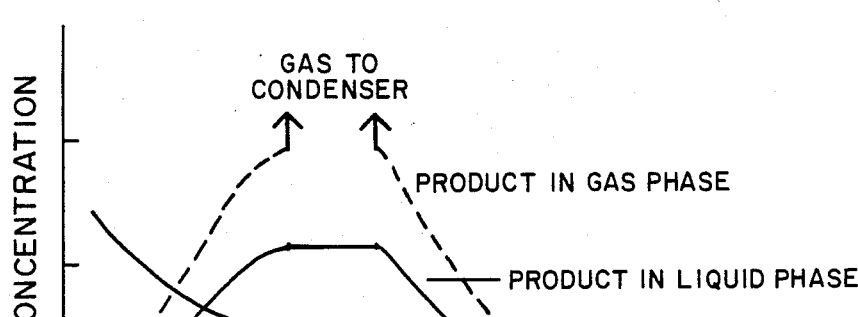
FIGURE 1

1

IMMOBILIZED CELL REACTOR-SEPARATOR WITH SIMULTANEOUS PRODUCT SEPARATION AND METHODS FOR DESIGN AND USE THEREOF

BACKGROUND OF THE INVENTION

1. Field of the Invention

This invention relates to a simultaneous fermentation/separation system (as well as apparatus and methods for use thereof) particularly useful in carrying out product inhibited fermentations such as in the bio-production of ethanol, acetone, acetic acid, butanediol, butanol or lactic acid. More particularly, this invention relates to a novel continuous cell reactor-separator which incorporates a unique four phase system design (e.g., (1) an inert stripping gas phase, (2) the liquid fermentation broth, (3) the solid reactor internals, and (4) the biological catalyst or cells), wherein any inhibitory metabolite is separated from the fermentation medium as soon as formed. In its preferred embodiments the continuous cell reactor-separator of this invention combines a co-current gas-liquid flow reactor system with a counter-current gas-liquid flow reactor system into a reactor design which produces a final effluent stream with both very low product and substrate concentrations, and a purified product stream containing no fermentation substrate or cells. In essence the preferred continuous cell reactor-separator system of this invention combine the advantages of a conventional plug reactor etc. reducing the liquid product concentration so that high reaction rates are maintained.

2. Description of the Problem and Prior Art

The production of inhibitory products or by-products during the course of a fermentation causes growth rates and reaction reaction rates to slow and eventually results in cell death. If the inhibitory compounds are removed as they are formed, then the reaction rates and cell viability can be maintained. Ethanol fermentation is a product inhibited reaction with a maximum final tolerable ethanol concentration ranging from 6 to 15% (W/V) depending upon the micro-organism. If the ethanol can be removed during the fermentation then high reaction rates and good substrate utilization can be assured. There have been several attempts to achieve this simultaneous separation-fermentation. Ramalingham and Finn (1977) and Cysewski and Wilke (1977) ran a continuous stirred tubular type reactor (CSTR) under vacuum. Spear (1981) suggested continuously withdrawing a portion of a fermenting mixture from a CSTR, flashing this stream to an ethanol enriched vapor output and ethanol depleted liquid which may then be returned to the reactor. Minier and Goma (1982) recently suggested a liquid extraction of ethanol using dodecanol in a pulsed cocurrent immobilized cell tubular reactor. They found rates increased by a factor of four and high sugar levels (400 gm/l) were well utilized. Herein we describe a gas-liquid separation in an immobilized cell bioreactor.

SUMMARY OF THE INVENTION

The basic Continuous Cell Reactor Separator (CCRS) is based on a four phase system design. The phases consist of (1) an inert stripping gas phase, (2) the liquid fermentation broth, (3) the solid column internals, and (4) the biological catalyst or cells. The liquid substrate solution and an inert gas phase are both introduced to the first "enriching" column of the two column reactor as shown in FIG. 1. The liquid and gas flow co-currently in the enriching column while the substrate is converted into the more volatile product by the cells. This product then is moved into the faster moving gas phase. At the end of the enricher the liquid phase goes to the top of the second "stripping" column and moves down counter currently to the gas phase introduced at the bottom of the stripping column. As the liquid moves down the stripper, the product is stripped into the gas phase while the cells are converting the remaining substrate to product. The CCRS allows nearly complete conversion of the substrate to product as the product liquid concentration will be low in the lower parts of the stripper so there will be little product inhibition of reaction rate.

In the immobilized cell CCRS either column can be run in either gas or liquid continuous flow regimes. FIG. 1 shows a liquid continuous stripper (gas bubbles up through the liquid and solid support of the enricher) followed by a gas continuous stripper (liquid dribbles down over the column packing in the gaseous environment). The graph at the bottom of FIG. 1 gives an idealized concentration profile of substrate, liquid product and gaseous product concentrations as a function of position in the CCRS. FIG. 1A shows a possible one column configuration for a design with both sections gas continuous. The choice of liquid or gas continuous depends on the relative reaction rates, separation efficiency and desired liquid residence time, in the CCRS.

If the CCRS is to be run with free cells, the configuration of FIG. 1 is followed with both columns being run as bubble columns. The cells in the exhausted feed may be recovered and recycled to the inlet of the enricher to ensure a high cell density if necessary.

A successfully operating Immobilized Cell Reactor Separator is demonstrated consisting of yeasts adsorbed to a natural sponge matrix and operated in the gas continuous mode. Very high reactor ethanol productivities were obtained with this reactor as well as good product separation. This constitutes an ethanol fermentation with immobilized cells operated in the gas phase continuous mode as well as the first immobilized cell reactor with gas phase product stripping. Operation in the gas phase continuous mode reduces liquid turbulence and this reduces the desorbing forces in the reactor. Operation in the gas continuous mode also allows free escape of the gas formed as a second product of the fermentation of sugars to ethanol. (Any highly absorbent matrix which has a "liquid hold-up" of between about 10% and about 40% and which does not prevent the requisite flow of the gas phase can be employed as a substitute for the sponge matrix herein described. "Liquid hold-up" as used herein is the volume fraction of the reactor actually containing liquid.)

The system designs of this invention include inter alia, the following embodiments:

(a) a four phase biological reactor-separator characterized by a cocurrent gas-liquid flow section section followed by a countercurrent flow section for the production of a volatile fermentation product from a nonvolatile substrate. This reactor is termed a Continuous Cell Reactor-Separator.

(b) a gas continuous immobilized cell reactor with the cells adsorbed to a sponge-like matrix termed an Immobilized Cell Reactor.

(c) a gas continuous immobilized cell reactor with the cells adsorbed to a sponge like matrix with simultaneous volatile product separation termed an Immobilized Cell Reactor Separator.

BRIEF DESCRIPTION OF THE DRAWINGS

FIG. 1 shows a schematic representation of a fermenter useful in practicing the invention, and a graph showing idealized concentration profiles of substrate and volatile product in both the liquid and gas phases in the fermenter sections.

DETAILED DESCRIPTION OF THE INVENTION

Figure 1A:
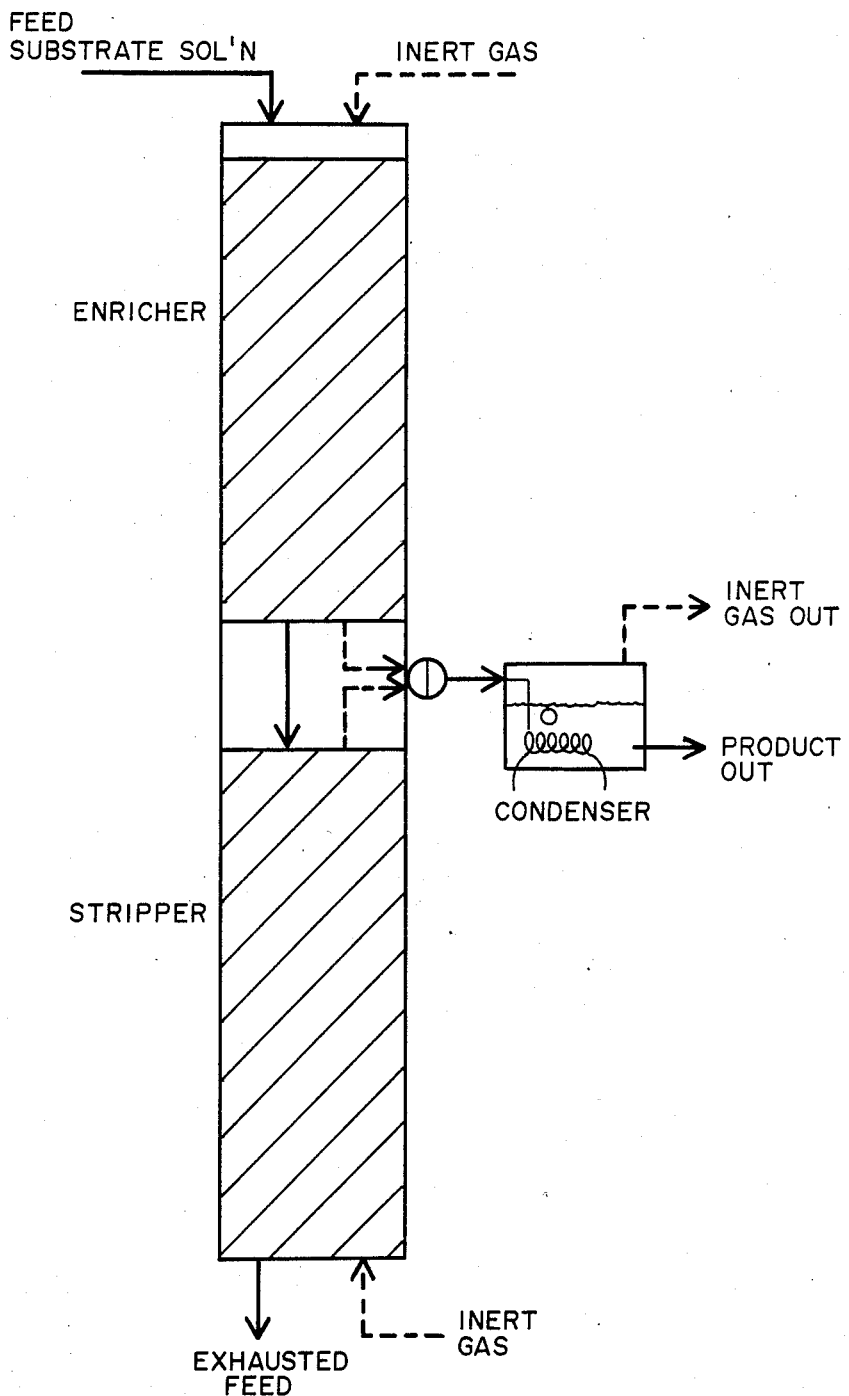
FIG. 1A shows a one column gas continuous reactor-separator useful in practicing the invention.

The Immobilized Cell Reactor Separator (ICRS) consists of two distinct columns in which the fermenting broth is contacted by both the immobilized cells and a 'stripping' gas phase. A basic schematic of the ICRS is shown in FIG. 1 along with idealized liquid and vapor compositions. The inlet substrate 1 and gas 2 move co-currently upwards the first or 'enriching column' 3 during which some fraction of the substrate 1 is converted to a volatile product by the cells. Some of the product moves into the gas phase following gas-liquid equilibrium. This gas phase 4 leaves the top of the enricher while the liquid phase 5 moves to the top of the second or stripping column 6. In this column 6 the liquid 5 moves down counter currently to the stripping gas 2. The remaining substrate in the liquid 5 is converted to product while the product is stripped into the gas phase 7 resulting in a final exhausted liquid feed effluent 8 containing, ideally, no substrate or product. Thus the ICRS both converts the substrate to product, and removes the product form the fermentation broth.

The gas phases 4 and 7 leaving the ICRS are condensed to recover the product 9 and inert gas 2.

METHODS AND MATERIALS

The organisms used in these studies were *C. pseudotropicalis*, IP 513, an ethanol tolerant lactose fermenting yeast described by Moulin, et al. (1980a, 1980b) obtained from the Institute pasteur, Paris, and *K. fragilis* 2415, a fast lactose fermentator described by Gawel and Kosikoski (1978) obtained from NRRL, Peoria, Ill.

GROWTH MEDIUM

The cells were grown from an agar slat at 31° C. for 48 hours in a medium containing 10 gm/l lactose, 3 gm/l yeast extract, 3 gm/l malt extract, 5 gm/l peptone in a shaker at 200 rpm. The feed was ultrafiltered (50,000 MW cutoff) whey made up from dried whey ultrafiltrate obtained from Food Ingredients, Inc., Elk Grove Village, Ill. This ultrafiltrate was then sterilized by passing it through a Gelman 0.2 $\mu$m filter.

ANALYTICAL METHODS

Lactose and ethanol were determined by liquid chromatography using a 6 mm×60 cm column packed with Aminex 50 W-X$^4$ at 85° C. (Ladish and Tsao, 1978). Cell density was determined microscopically using a Petroff-Hausser cell counter, turbidimetrically by measuring OD at 420 nm, and gravimetrically by centrifugation and rinsing the cells twice with distilled water, drying for 24 hours on a hot plate at 110° C.

The Bioreactor

Figure 2:
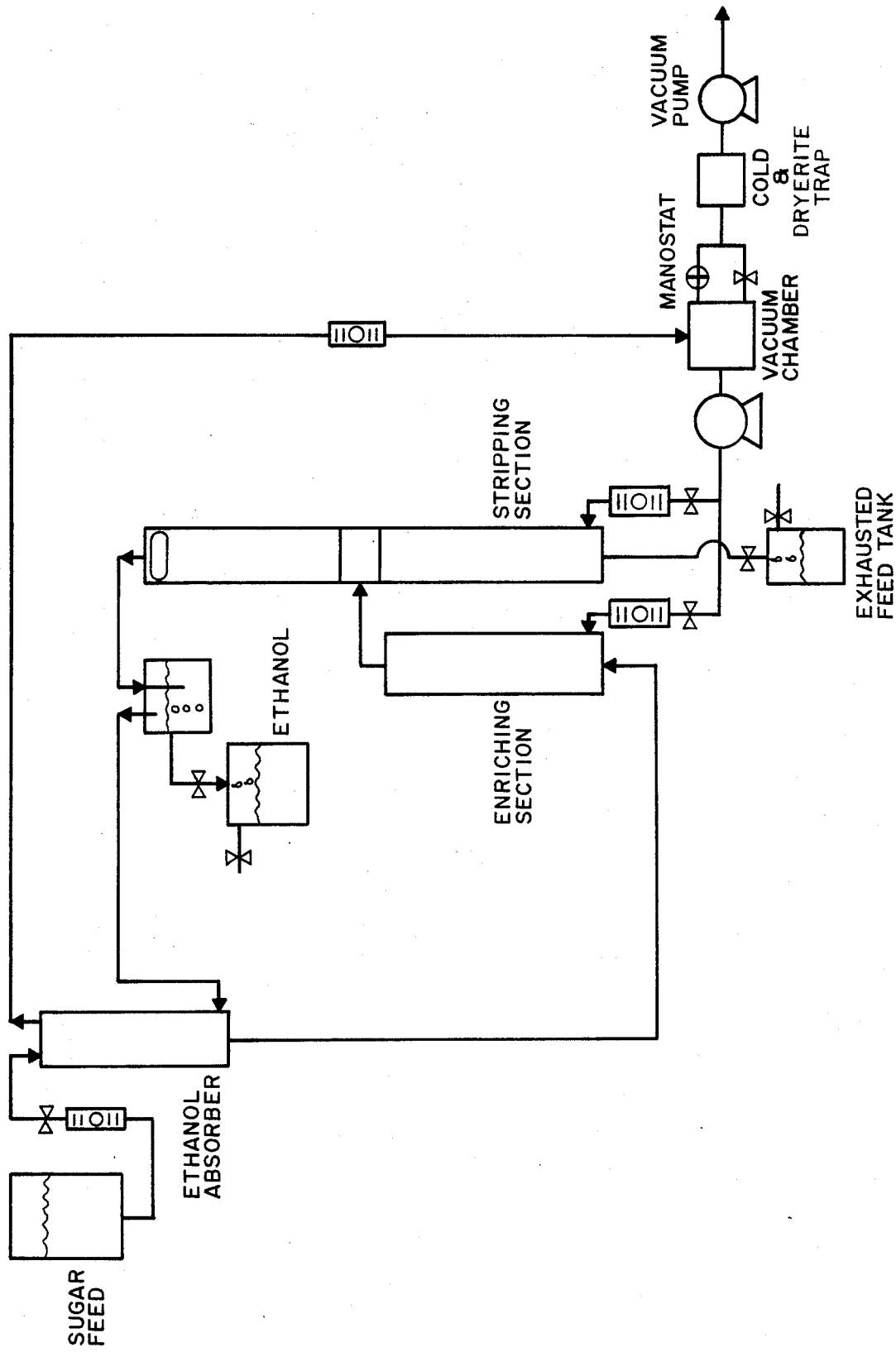
FIG. 2 shows another reactor-separator system.

The ICRS consists of two columns packed with $\frac{1}{4}''$ ceramic Intalox saddles (Norton Co.), a standard gas-liquid contacting packing. The saddles were coated with 25% gelatin crosslinked by gluteraldehyde (Sitton and Gaddy, 1980; Griffith and Conpere, 1975) to facilitate adsorption of the yeast. A cell suspension was added to the reactor and the cells immobilized by adsorption. FIG. 2 shows a diagram of the complete reactor-separator apparatus. The enricher section is a jacketed plexiglass column 95 cm high and 7.5 cm in diameter, and the stripping section is 120 cm high and 7.5 cm in diameter. Four sampling ports are situated in both enricher and stripper. The packed height of the enricher is 85 cm., and the stripper 105 cm. The void fraction of the packed reactor is 0.65 with a gas fraction of 0.06–0.10 in the liquid continuous mode as determined by draining the reactor. The gas from the condenser is contacted with the feed to reduce the ethanol concentration in the gas as well as to humidify the gas.

Reactor Modeling

Stationary Adsorbed Microbial Populations Modeling

Figure 3:
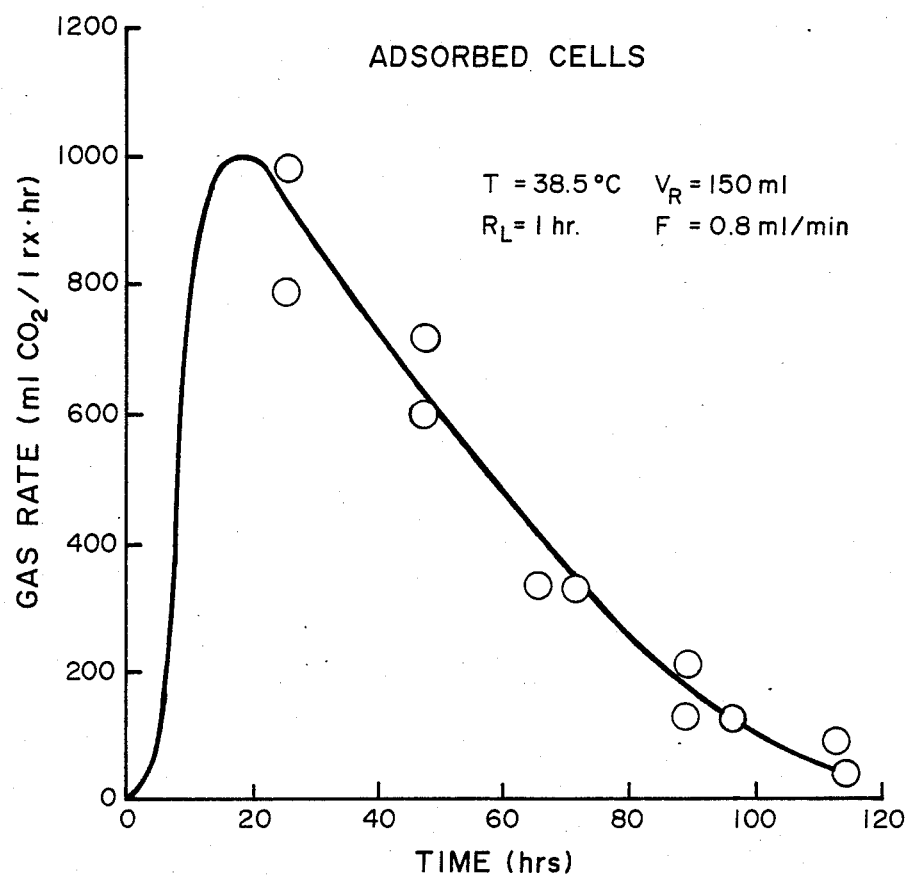
FIG. 3 shows the rate of absorption of cells with various gas flow rates.

An adsorbed population of living microbes must carry on all cell processes of growth, maintenance, reproduction or budding, and death. If the bonding between the cells and the adsorbing surface is very strong then the cells will remain attached to the surface indefinitely. After all available binding sites in a reactor are occupied by cells then there will be a slow loss of total activity as the cells die but remain attached to the surfaces in the reactor. This is a non-steady state reactor as the number of live, adsorbed cells will increase until all sites are filled, and then decrease as death occurs. This sort of behavior is shown in FIG. 3 which was obtained by absorbing yeast to ceramic following the procedure of Marcipar, et al., (1978). To obtain a stable and stationary population some fraction of the absorbing surface must be cleared, allowing new young cells to adsorb. To model this process we can adapt the theory of surface renewal as developed by Dankwertz (1951,1955) for mass transfer from surfaces of liquids.

If we assume that there is some fraction of the total adsorbing surface that is randomly swept clear in some unit period of time and that the chance of any surface element being cleared is independent of how long it has been since it was last cleared then we can define R as being the fractional rate of replacement of the surface elements of all age groups. Defining $\phi(\tau)d\tau$ as the area of surface elements with an age between $\tau$ and $\tau+d\tau$, then for a unit adsorbing surface area we can integrate over elements of all ages;

$$1 = \int \phi(\tau)d\tau \qquad [1]$$

solving for the age distribution ($\phi(\tau)$) of the surface elements as a function of the renewal rate R gives (Dankwerts, 1955);

$$\phi(\tau) = \int Re^{-R\tau} \qquad [2]$$

The fermentative activity of an element of the surface is a function of the number of live cells attached to the surface element, which is in turn a function of the age of that surface element. If we define $S_{s1}$ as the number of adsorbed and alive cells per unit area, $X_{s1}$ will decrease as the age ($\tau$) of an element increases. The average fermentation rate can be determined by integrating over elements of all ages.

$$\hat{r}_p = \int_0^\infty X_{s1}(\tau)\nu(T,P,S)\phi(\tau)d\tau \qquad [3]$$

where $\nu(T,P,S)$ is defined as:

$$\nu(T,P,S) = \nu_{max}(T)\left[\frac{S}{S+K_s}\right]\exp(-K_p P) \qquad [4]$$

and the number of live cells per unit area ($X_{s1}$) decays following a standard exponential death rate:

$$X_{s1} = X_{so}\exp(-Kd\tau) \qquad [5]$$

Equation 5 is based on the assumption that the cleared area is immediately filled with young cells at a surface density $X_{so}$. Integrating Equation 3 then gives:

$$\hat{r}_p = X_{so}\nu(T,P,S)\left(\frac{R}{R+Kd}\right) \qquad [6]$$

examining Equation 4 we see that as the surface renewal rate R goes to zero the total rate $\hat{r}$ also goes to zero which is what is shown in FIG. 3, and is what one would expect as the cells die and are not replaced. We also see if Kd→0 (i.e., cells don't die) the activity remains at its original rate which is also what would be expected. So from this analysis we see the importance of the renewal rate being higher than the death rate.

The renewal rate R will be affected by the strength of the absorbing bonding and the strength of the de-sorbing forces, i.e., the degree of shear stress on the surface. Rittman and McCarthy (1980) developed a model for a steady state biological film thickness based on a balance of growth and decay. Rittman (1982) included film loss due to shear forces and determined that the film loss rate was equal to the amount of biomass in the film multiplied by the shear stress to the 0.58 power if the film was under 0.03 cm. thick. Yeast adsorption is not a film phenomena however; photomicrographs by Sitton and Gaddy (1980), Bandyopadhyay and Ghose (1982) show a unicellular type of distribution on the surface of the support. Dudderidge et al (1982) show that a shear stress of over 10 n/m² prevented attachment of bacteria to a stainless steel surface.

The death rate constant (Kd) is generally found to follow an Arrhenius type increase with temperature as is the specific productivity $\nu_{max}$. If R is determined and the effect of temperature on the renewal rate R is small then the optimal operating temperature can be solved for by maximizing $r_p$ (Eq. 6) as a function of T if the temperature kinetics of death and productivity are known.

Plug Flow Immobilized Cell Reactor

Yeast attached to a solid support in a tubular reactor can be considered as a 'biological catalyst' and we can write a mass balance for yeast, substrate and product for a plug flow heterogenous reactor at steady state as:

$$v\frac{dX}{dz} = Sg\,\hat{r}_x \qquad [7]$$

$$v\frac{dS}{dz} = Sg\,\hat{r}_s \qquad [8]$$

$$v\frac{dP}{dz} = Sg\,\hat{r}_p \qquad [9]$$

where v is the fluid linear velocity; Sg is the surface to volume ratio of the packing in the reactor; and r is the reaction rate per unit area.

These balances are based on the assumptions
1. Constant density fluid
2. No axial dispersion
3. Steady state
4. Reaction occurs only on surface of the packing Various expressions for specific growth rate of cells and specific productivity rate of ethanol have been proposed but for this study we will use the rate expressions proposed by Aiba, et al., (1968).

$$\mu = \mu_m \exp(-K_p P)\frac{S}{K_s + S} \qquad [10]$$

As ethanol production and substrate utilization are growth associated we should be able to write:

$$r_x = k_1 r_p = -k_2 r_s \qquad [11]$$

However, it has been noted that fermentation can occur at ethanol levels where growth is stopped (Aiba et al, 1968) so $k_1$ and $k_2$ are not always the same. In this study we are mainly interested in ethanol production rather than yeast production so we can write:

$$\hat{r}_p = X_s \nu_{max} \exp(-K_p P)\frac{S}{K_s + S} \qquad [12]$$

$$\hat{r}_s = -k_1 r_p \qquad [13]$$

-continued $$\hat{r}_x \cong k_2 r_p \quad [14]$$

The saturation constant $K_s$ is generally less than 1 g/l so assuming that the sugar level is well over 1 g/l we can write:

$$\frac{dP}{dz} = \left(\frac{SgX_s\nu_{max}}{\nu}\right) \exp(-Kp\, P) \quad [15]$$

Integrating, we have:

$$\left(\frac{SgX_s\nu_{max}}{\nu}\right) Z = \frac{1}{Kp}(\exp(+Kp\, P) - 1) \quad [16]$$

Figure 4:
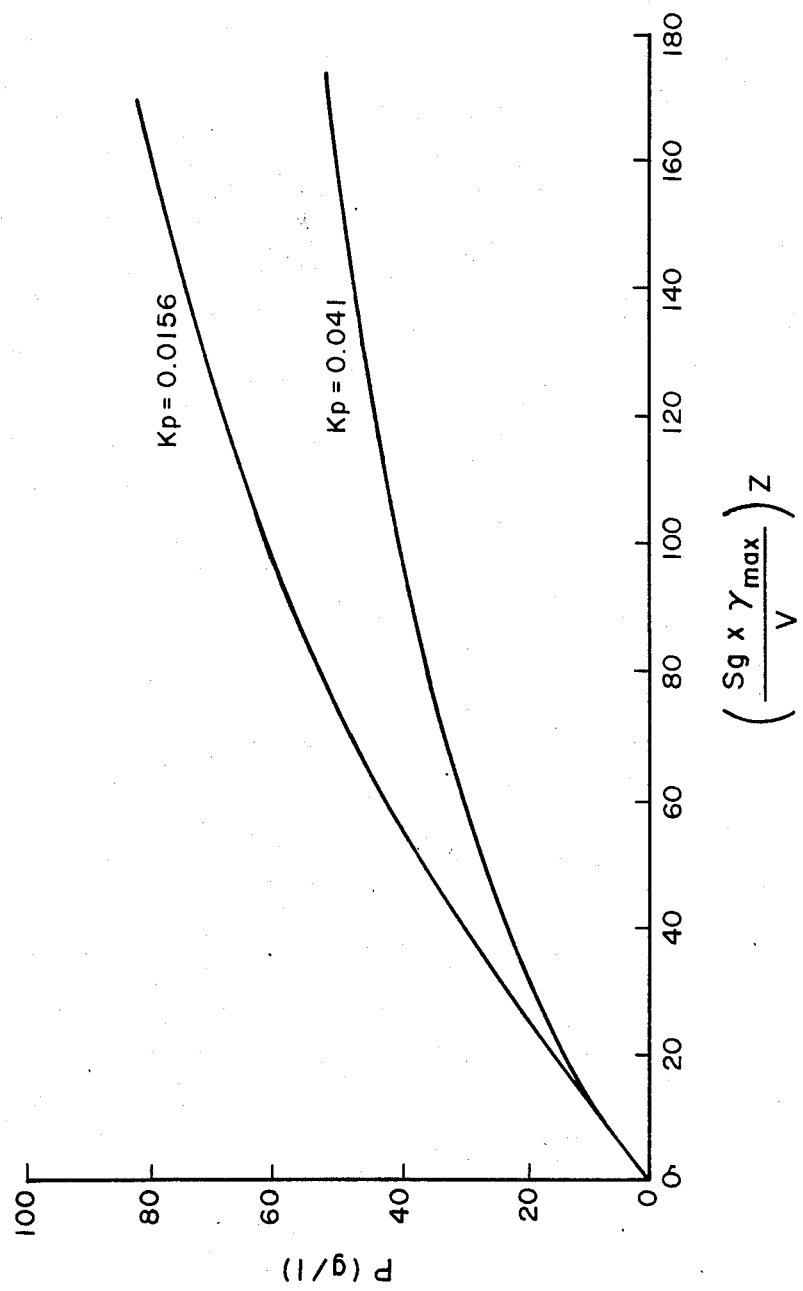
FIG. 4 shows ethanol concentration profiles in a reactor of the invention.

This relation is shown in FIG. 4 with Kp=0.0156 (data from Moulin (1980b) for *Candida pseudotropicalis* 513) and Kp=0.041 (experimental data for *Kluvermyces fragilis* 2415). The important effect of ethanol inhibition is readily seen from this figure. A dimensionless reactor length of 160 is needed to produce 50 g/l ethanol using *Kluvermyces fragilis* 2415 (Kp=0.041) while with the less inhibited *Candida pseudotropicalis* 513 a dimensionless reactor length of 72 will give 50 g/l ethanol. This model (Eq. 10) is inaccurate as the assumptions of no axial diffusion and constant density are violated when $CO_2$ is produced and bubbles up through the reactor, and there is some reaction in the fluid phase due to free yeasts. However, the model does describe the actual concentration profiles of immobilized cell reactors fairly well as the results of Sitton and Gaddy, (1980); Gencer, et al., (1980) and Ghose and Bandyopadhyay (1980) indicate.

Tyagi and Ghose (1982) show a more detailed mathematical description of an ICR including axial dispersion, free cell production and activity and substrate inhibition which they solve numerically. They treat the $CO_2$ as a constant volume inert phase within the reactor similar to the packing.

Two Phase Immobilized Cell Reactor

In the ICRS, however, the gas phase must be accounted for. Making a steady state component balance for an individual differential element gives us;

$$\text{accum} = \frac{dC}{dt} = 0 = (V_i y_i - V_o y_o) + \quad [17]$$

$$(L_i x_i - L_o x_o) + dV\, Sg\, \hat{r}_c$$

The solution of this set of equations in a finite difference form is difficult even without the reaction term (Rasquin, et al., 1977). Therefore, a stage-equilibrium approach was used with the height equivalent of a theoretical plate (HETP). Assuming gas-liquid equilibrium we have the same equation (17) but with dV being the volume of the whole stage. Furthermore, we use the assumption that the liquid and vapor leaving the stage are in equilibrium which gives us an added relation and allows the whole system to be solved.

Eckert (1979) shows that the HETP varies only slightly with vapor rate for distillation systems. The flooding vapor velocity is that vapor rate that 'blows' the liquid back out the top of the column. Column heights are determined based on the desired number of theoretical plates. The column diameter should be at least 12 to 20 times the size of the packing so that the liquid flow down the walls of the column is not a major fraction of the total liquid flow. The actual required column diameter is determined based on the desired pressure drop, the gas and liquid densities and flow rates, and a design chart obtained from the manufacturer (Norton Co., 1975). The cross-sectional area of the column is then determined based on the total gas flow rate. For the ¼ inch Intalox saddle the height of a theoretical plate is about 5 inches (Eckert, 1979) but may be different in our application.

Vapor-Liquid Equilibrium

The basic liquid-vapor equilibrium between the gas mole fraction ($y_i$) and the liquid mole fraction ($x_i$) for water and ethanol as a non-ideal solution and gas can be described as (Chao and Greenkorn, 1978):

$$y_i = \frac{\overline{P}}{P_t} = \frac{Y_i x_i P_i^p}{O_i} \quad [18]$$

The vapor pressure of the pure components $CO_2$, $H_2O$ and ethanol can be written according to the Clausius-Clapyron relation of P and T:

$$P_i^p = \exp\left[\frac{a}{T} + b\right] \quad [19]$$

where T=absolute T(°K.) and a and b for the components were determined by curve fitting data obtained from the CRS Handbook of Chemistry and Physics.

|        | a     | b     |
|--------|-------|-------|
| $CO_2$   | −1979 | 17.42 |
| $H_2O$   | −5294 | 20.93 |
| ethanol | −5084 | 21.10 |

The fugacity coefficient ($O_i$) approaches 1.0 as the pressure decreases. Even at atmospheric pressure and 100 C. the fugacity coefficient varies from 1.0 by less than 1% (Andiappan and McLean, 1972), so the fugacity coefficient was not included in these calculations.

The activity coefficients for ethanol ($Y_1$) and water ($Y_2$) can be expressed by a modified Van-Laar equation (Black, 1959):

$$\log Y_1 = \frac{A_{12}}{\left[1 + \frac{A_{12} x_1}{A_{21} x_2}\right]^2} \quad [20]$$

$$\log Y_2 = \frac{A_{21}}{\left[1 + \frac{A_{21} x_2}{A_{12} x_1}\right]^2} \quad [21]$$

where $A_{12}$ and $A_{21}$ were determined as inverse functions of temperature from data presented by Black and Ditsler (1972)

$$A_{12} = \frac{-.0168 \times 10^4}{T} + 1.21 \quad [22]$$

$$A_{21} = \frac{.0075 \times 10^4}{T} + .1919 \quad [23]$$

The resulting vapor-liquid equilibrium curves compared well to data collected by Beebe et al (1942).

Reactor Design Calculations

The calculations for reactor design may be divided into two parts; the enriching section and the stripping section.

a. Co-current Enriching section

A basic component mass balance is solved for each component. As there is a reaction, the liquid and vapor flow rates change from the stage to stage. A balance on stage j gives:

$$l(i,j-1) + v(i,j-1) + V^* \frac{IN}{gen(i)} = \frac{OUT}{l(i,j)} + v(i,j) \quad [23]$$

Using the equilibrium liquid vapor relationship:

$$Y_i = \frac{v(i,j)}{V_{T(j)}} = K x_i = \frac{K \, l(i,j)}{L_{T(j)}} \quad [24]$$

we can solve for l(i,j) from equation (24) giving:

$$l(i,j) = \frac{l(i,j-1) + v(i,j-1) + gen(i)^*V}{1 + K \, V_T/V_L} \quad [25]$$

but as $V_T$ and $V_L$ are not initially known these equations must be solved iteratively.

b. Stripping Section

In the counter current stripping section of the reactor we have a difficult system to solve as the reaction rate on each stage is affected by the composition of the stage above and below. Nelson (1971) suggested a matrix method for solving this sort of problem utilizing a Newton-Raphson convergence approach to determine temperature and vapor flow rates similar to the approach of Tierny and Bruno (1967) but used the method of damped least squares as a convergence check. They were successful but the convergence was non-monotonic suggesting that instabilities could well develop and the method requires a great number of partial derivatives to be calculated at each iteration. In this study we used the relaxation procedures of Jelinek, et. al. (1973, 1976) with good results solving the transient mass balance equation:

$$U_j \frac{dx_{i,j}}{dt} = L_{j-1} x_{i,j-1} + V_{j+1} y_{i,j+1} - \quad [26]$$

$$[V_j y_{i,j} + L_j x_{ij}] + \hat{r}(x_{i,j}) \cdot A_s$$

Where $U_j$ is the total moles of the stage which is approximated by the liquid molar holdup. The derivation is then written in finite difference form:

$$\frac{dx_{i,j}}{dt} = \frac{x_{i,j}t + 1 - x_{k,j}t}{\Delta t} \quad [27]$$

with a finite difference term w defined as $(\Delta t/U_j)$. Jelinek (1973) suggests using a value for w between 1 and 1000. We found quick (15-20 iterations) monotonic convergence using a value of 10 for w. The system of finite difference equations is written in matrix form and the Thomas algorithim is used to solve for liquid mole fractions.

Results

The immobilized cell reactor characteristics were first determined with no separation. Table 1 gives the operating characteristics for a small ICR (600 ml) after steady state conditions were achieved (approximately 10 days) for Kf 2415 and Cp 513. These results were then used to determine the parameters for the model. The model is based on the actual lab apparatus in size and internals as described in the materials section with 7 equilibrium stages in both the enricher and stripper.

TABLE 1

| Immobilized Cell Reactor Performance | |
|---|---|
| C. pseudotropicolic 513 | K. fragilis 2415 |
| F = 21.5 ml/hr | F = 15.6 ml/hr |
| $S_o$ = 28 gm/l | $S_o$ = 24 gm/l |
| $P_o$ = 34 gm/l | $P_o$ = 35 gm/l |
| $t_r$ = 14.3 hr | $t_r$ = 19.2 hr |
| $v_{av}$ = 2.4 gm/l hr | $v_a u$ = 1.8 gm/l hr |

Effect of Separation

Figure 5:
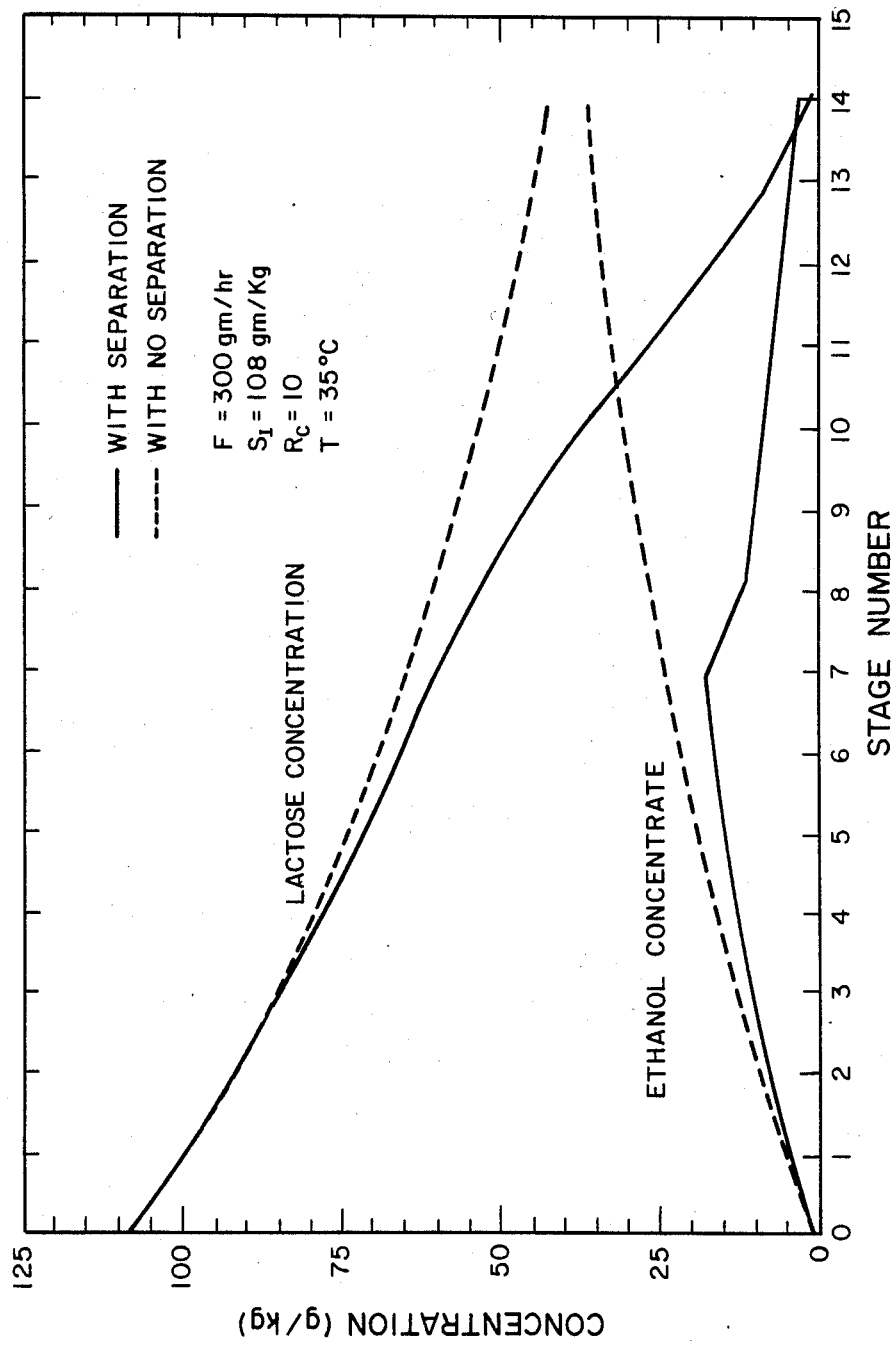
FIG. 5 shows expected lactose and ethanol concentrations in a reactor-separator with and without gas phase separation of the product.

FIG. 5 shows the lactose and ethanol (liquid phase) profiles in the ICRS with and without separation. The dotted lines show a standard sort of ICR curve with an initial inlet lactose concentration of 108 gm/liter being reduced to 42 gm/liter. If the same reactor is run with separation (gas recycle ratio $R_c$=10 moles $CO_2$ recycled/mole produced by reaction, P=70 mm) we see that reaction is carried close to completion with an outlet lactose concentration of only 1.7 gm/l. The ethanol has been almost completely removed as well with an outlet ethanol concentration of less than 2 gm/l meaning that 97% of the ethanol produced has been removed from the liquid phase and condensed in the condenser, and the ethanol concentration in the liquid phase is under 18 gm/Kg at all points in the reactor. The final effluent from the reactor contains any salts in the feed, cells and less than 2 gm/l lactose or ethanol. The BOD of the whey has been reduced to about 2.5% of its original value. Slower flows (longer residence time) and a higher $CO_2$ recycling rate could reduce the outlet ethanol and lactose concentrations even further if desired.

Thus we see that by separating the ethanol as it is produced the same reactor was able to improve its sugar utilization from 62% to 98%, given an outlet exhausted feed low in broth lactose and ethanol, and give a 'pure' ethanol-water product stream of 139% ethanol (w/w).

Effect of ICRS Operating Temperature

Figure 6:
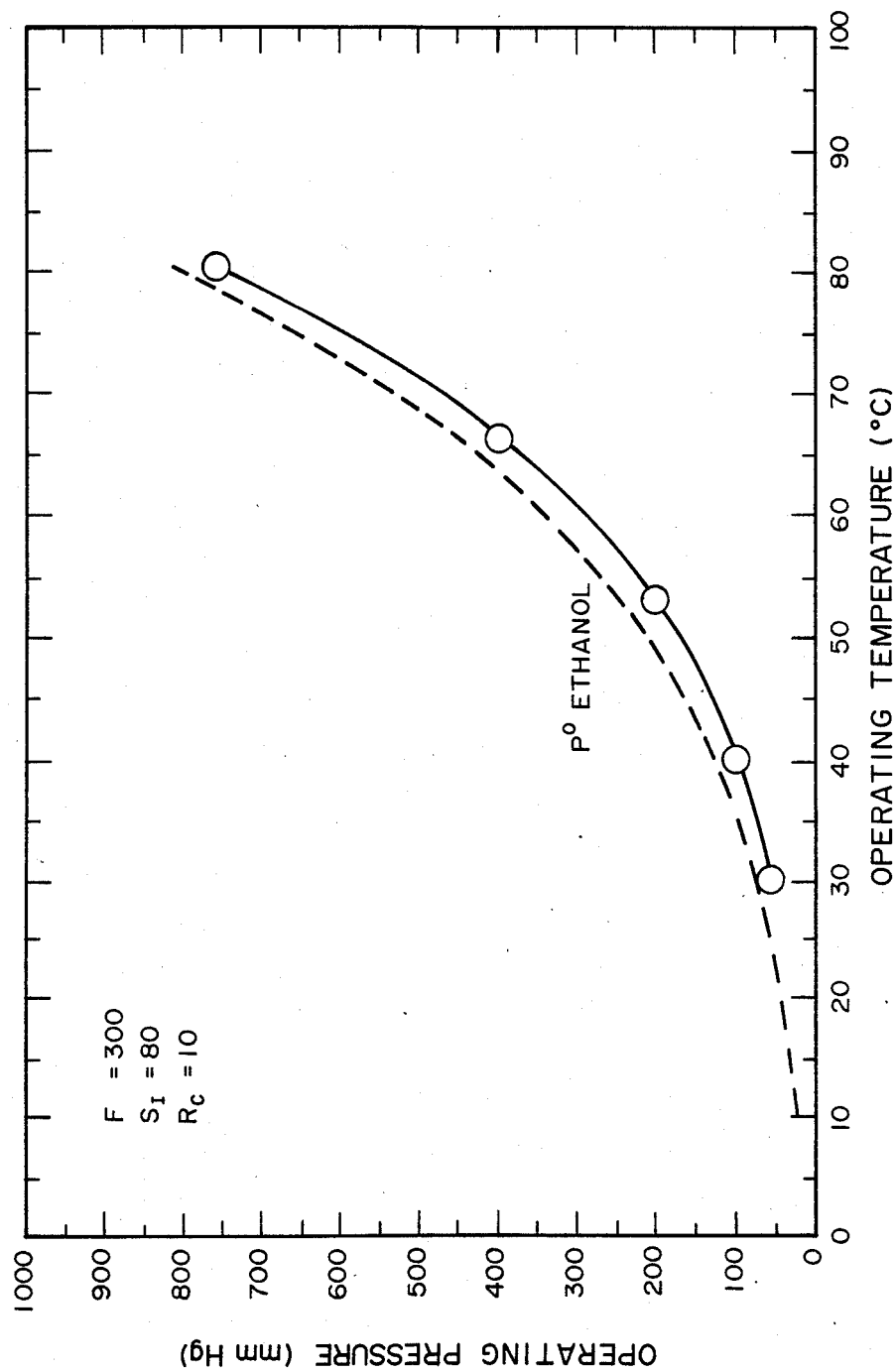
FIG. 6 shows the effect of operating temperature on the reactor-separator required operating pressure.

The degree of vacuum needed to achieve a satisfactory separation with a given gas recycle ratio depends on the operating temperature of the reactor. If the fermentation rate is assumed constant at the rate it actually gives at 32° C. for all temperatures, then we can solve for the temperature that will give a desired outlet ethanol concentration. This was done for a base case of: feed rate=300 gm/hr; inlet lactose concentration=80 gm/l; outlet ethanol concentration between 2 and 3 gm/l; outlet lactose concentration between 7 and 10 gm/l; gas flow rate ratio $R_c$=10 moles $CO_2$ recycle/moles produced by reaction with 90% of the gas directed up the stripping column. As shown in FIG. 6, we found that at 30° C. an operating pressure of 60 mm is required while at 53° a pressure of 200 mm is satisfactory until finally at 80° C. no vacuum is required at all. The required operating pressure closely follows the vapor pressure of pure ethanol as shown by the dotted line in FIG. 6.

Thus it is clear that if a microbe can be found or developed to ferment sugars to ethanol at high temperatures the degree of vacuum required can be reduced at any given gas recycle ratio.

Effect of Gas Flow Rates

Figure 7:
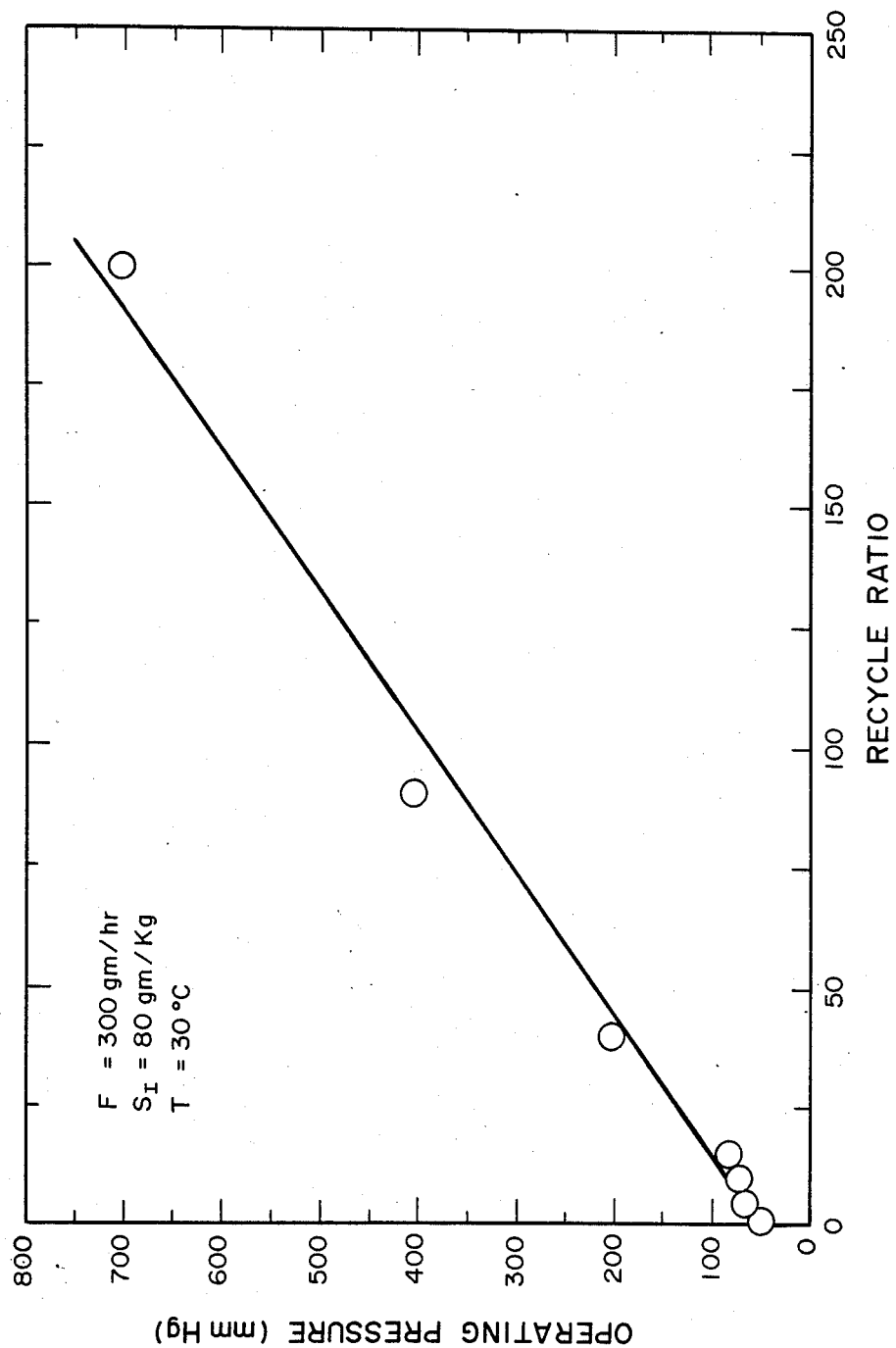
FIG. 7 shows the effect of gas flow rate (gas recycle ratio) on the required operating pressure at a constant temperature.

The volatile product can be removed either by reducing the pressure at a given gas flow rate or by increasing the gas flow rate at a given pressure. The necessary gas flow rate to achieve a final effluent ethanol concentration of between 2 and 5 gm/l at 35° operating temperature (with the same base conditions as above) at different pressures was determined and the results are shown in FIG. 7. There seems to be a roughly linear relationship between the operating pressure and the required recycle ratio $R_c$. We see that the required gas recycle ratio R goes to zero at about 50 mm at which point the reactor will actually be boiling. The farther operating limit, atmospheric pressure (760 mm), requires a recycle ratio of over 200 to achieve the desired separation. Reasonable recycle ratios ($R_c<20$) occur at operating pressures of under 125 mm although the choice of operating pressure and recycle ratio must involve trade-offs between required vacuum and required gas recycling; an economically optimal pressure and $R_c$ could be solved for given costing economic data.

NOMENCLATURE (Employed Hereinabove)

$A_{ij}$ = modified Van-Laar coefficents
$A_s$ = reacting surface area per stage (dm$^2$)
F = feed rate (gm/hr)
kd = death rate constant (hr$^{-1}$)
kp = ethanol inhibition constant (l/gm)
Ks = substrate saturation constant (gm/l)
$L_T$ = total moles liquid leaving stage
P = product (ethanol) concentration (gm/l)
$P_{op}$ = operating pressure (mm Hg)
R = renewal rate (Hr$^{-1}$)
$R_c$ = CO$_2$ recycle ratio $$\left( \frac{\text{moles CO}_2 \text{ recycled}}{\text{mole CO}_2 \text{ produced by } rx} \right)$$

$\hat{r}$ = reaction rate per unit area reacting surface (gm/dm$^2$ hr)
$\hat{r}_p$ = rate of product formation (gm/dm$^2$ hr)
$\hat{r}_s$ = rate of substrate utilization (gm/dm$^2$ hr)
$r_x$ = rate of cell formation (gm/dm$^2$ hr)
S = substrate concentration (gm/l)
$S_g$ = surface area to volume ratio of reactor packing (dm$^{-1}$)
$S_I$ = inlet substrate concentration (gm/l)
$S_o$ = outlet substrate concentration (gm/l)
T = temperature (OK)
t = time (hr)
V = fluid linear velocity (dm/m)
v(i,j) = vapor molar flow of component i leaving stage j
$V_T$ = total moles vapor leaving stage
$X_s$ = concentration of cells on surface of packing (gm/dm$^2$)
$X_s$ = concentration of adsorbed live cells on surface (gm/dm$^2$)
$X_{so}$ = maximum concentration of adsorbed cell on surface (gm/dm$^2$)
Z = reactor length (dm)
l(i,j) = liquid molar flow of component i leaving stage j

Greek $\mu$ = specific cell growth rate (gm cell/gm cell hr)
$\mu_m$ = maximum specific rate (gm cell/gm cell hr)
$\nu$ = specific productivity rate (gm product/gm cell hr)
$\nu_{max}$ = maximum specific productivity rate (gm product/gm cell hr)
$\phi(\tau)$ = age distribution function
$\tau$ = element age (hr)

NOMENCLATURE (Employed Hereinafter).

Dax = axial dispersion coefficient cm$^2$/s
$G_E$ = gas/liquid molar flow ratio in the enricher
$G_{st}$ = gas/liquid molar flow ratio in the stripper
kd = death rate constant (hr$^{-1}$)
kp = product inhibition constant (l/gm)
Kg = substrate saturation constant (gm/l)
L = liquid flow rate
P = product (ethanol) concentration (gm/l)
$P_o$ = outlet ethanol concentration (gm/l)
Pe = Peclet number (Lu$_L$/Dax)
R = surface renewal rate (hr$^{-1}$)
$\hat{r}$ = surface reaction rate
S = substrate concentration (gm/l)
$S_I$ = inlet substrate concentration
$S_o$ = outlet substrate concentration
$U_g$ = superficial gas rate (cm/sec)
$U_L$ = superficial liquid rate (cm/sec)
$X_{so}$ = surface density of cells (gm/dm$^2$)

Greek $\nu$ = ethanol productivity (gm/l hr)
nu$_{max}$ = maximum ethanol productivity The simultaneous separation of volatile fermentation products from product inhibited fermentations can greatly increase the productivity of a bioreactor by reducing the product concentration in the bioreactor, as well as concentrating the product in an output stream free of cells, substrate or other feed impurities. The immobilized cell reactor-separator (ICRS) consists of two column reactors: a co-current enriching column followed by a countercurrent stripping column. The columns are 4 phase tubular reactors consisting of (1) an inert gas phase, (2) the liquid fermentation broth, (3) the solid column internal packing, and (4) the immobilized biological catalyst or cells. The application of the ICRS to the ethanol from whey lactose fermentation system has been investigated as a function of gas flow rate and operating pressures. Operation in the liquid continuous or bubble flow regime allows a high liquid holdup in the reactor and consequent long and controllable liquid residence time but results in a high pressure drop over the length of the reactor and low gas flow rates. Operation in the gas continuous regime gives high flow rates and low pressure drop but also results in very short liquid residence time and incomplete column wetting at low liquid loading using conventional gas-liquid column packings.

Using cells adsorbed to conventional packing ($\frac{1}{4}''$ Intalox saddles) it was found that a good reaction could be obtained in the liquid continuous mode, but little separation, while in the gas continuous mode there was little reaction but good separation. Operation of the ICRS with a liquid continuous enricher and gas continuous stripper was therefore more of a reaction followed by separation than simultaneous reaction and separation.

Using cells adsorbed to an adsorbant column packing matrix allowed operation in the gas continuous regime with a liquid hole up of up to 33% of the total reactor volume. High reaction rates and good product separation were obtained using this matrix. High reaction rates were obtained due to high cell loading in the reactor. A dry cell density of nearly 100 gm per liter reactor was obtained in the enricher. The enricher ethanol productivity ranged from 50 to 160 gm/l hr while the stripper productivity varied form 0 to 32 gm/l hr at different feed rates and concentrations. A separation efficiency of 98% was obtained from the system running with an enricher gas/liquid mole flow ratio of 2.7 and a stripper gas flow ratio of 5.2.

In gas-liquid reactors the flow regime depends on the relative gas and liquid velocities. A low liquid rate combined with a high gas rate gives gas continuous or "trickle column" operation while conversely a low gas rate gives a liquid continuous or "bubble column" operating regime. The choice of operating regime depends upon many factors. If the primary concern is separation, then good gas-liquid contact is the major consideration and operation in the spray or pulse flow regime is probably best. In fact most packed column adsorption and distillations are operated in this "high interaction" region. The standard column design methods for these separations involves operation near the maximum gas and liquid rates possible. This maximum rate is termed the "flooding" point where the gas actually blows the liquid out of the column. Usual design methodology calls for determining the gas flow rate that will give flooding at a given liquid flow rate, and then using 0.5–0.7 of this rate to determine column diameter. Column height is then determined using a mass transfer or theoretical stage analysis.

However, in a case where a reaction is involved either on the packing surface or in the bulk gas or liquid phase, the choice of operating flow regime may be more influenced by factors relating to the reaction—liquid and/or gas residence time, completeness of liquid solid contact, etc.

In the case of the ICRS with adsorbed cells acting as a surface catalyst the reaction rate is limited to the speed at which the cells can adsorb and metabolize the nutrient carbohydrate source. The basic choice of operating in a gas or liquid continuous mode on a standard column packing is influenced by the following factors.

The bubble column has the advantages of:
1. high liquids fraction in the reactor. This allows a long and controllable liquid residence time permitting the relatively slow fermentation to go to completion.
2. complete contact of the packing surface and attached cells with the fermentation broth.

But the disadvantages of:
1. high pressure drop over the length of the column due to the liquid head. This can result in a large difference in gas-liquid volatility and solubility at different points in the reactor as well as differences in gas rates due to expansion of the gas.
2. large degree of liquid phase axial dispersion. Bubble columns have liquid dispersion coefficients ranging from 20–900 cm$^2$/sec with the degree of axial dispersion strongly correlated to the column diameter and gas rates indicating problems in scale-up.
3. large degree of liquid turbulence at higher gas flow rates may lead to high shear rates, cell desorption, and foaming.
4. low gas flow rates. The low gas flow rates required for bubble column operation may be insufficient to achieve the desired separation or to supply adequate gas phase reactants or nutrients to the reactor.

Trickle column or gas phase continuous operation has the advantages of:
1. low pressure drop and high gas rates. The high gas flow rates and fairly constant pressure conditions in a gas continuous ICRS allow adequate gas flow for product stripping so that a good separation is possible.
2. low shear. As the liquid is merely trickling down over the surface packing the shear rate is low, which should prevent desorption of microbes.
3. low axial mixing. The axial mixing is greatly reduced as there is no actual liquid flow up the column, (unless one is in the spray or pulse flow regime) merely some differing rates of downwards flow.

With the disadvantages of:
1. short liquid residence time. The liquid residence time is short as the total liquid volume or holdup is minimal on standard packings. There may also be channeling of trickles further reducing residence time and reducing liquid solid contacting.
2. incomplete packing wetting. The degree of wetting is closely related to the liquid loading rates. At low or trickle column conditions the wetting may be as low as 5 to 10% of the total packing surface area.

For adsorbed cell systems with foaming substrates, gas-liquid flow regimes involving surging, spray, or turbulent phase interaction must be avoided as the shear forces will desorb cells in adsorbed cell system and the foam generation will quickly lead to a completely foam filled system. Thus for whey and many other fermentation broths which have a high foaming propensity we are practically restricted to homogeneous bubble flow regime ($u_g < 0.025$ m/sec) or to trickle flow ($L < 0.1$ $L_{flood}$).

The use of liquid adsorbing column packing to increase the wetted surface area was suggested by Linek, et al (1974), who coated plastic packing with a hydrophilic salt layer. This increased the wetted area of the plastic packing 25 times to the same wetted area as similarly sized ceramic packing. Going one step farther, the use of a naturally water adsorbant packing with a high liquid retaining capacity should allow operation in the gas continuous regime while retaining a sizable liquid hold up and reduce problems of liquid channeling.

Methods and Materials

The organism used in these studies was *K. fragilis* 2415, a fast lactose fermentator described by Gawel and Kosikowski (1978) obtained from NRRL, Peoria, Ill. The ceramic packed bioreactors were sterilized by passing live high pressure steam through the reactor for 1 hour, while the adsorbant packing columns were sterilized by running 8% formaldehyde through the column for 24 hours at 40° C.

Growth Medium

The cells were grown from an agar slat at 31° C. for 48 hours in a medium containing 10 gm/1 lactose, 3 gm/1 yeast extract, 3 gm/1 malt extract, 5 gm/1 peptone in a shaker at 200 rpm. The feed was ultrafiltered (50,000 mw cutoff) whey made up from dried whey ultrafiltrate obtained from Food Ingredients, Inc., Elk Grove Village, Ill. This ultrafiltrate was then sterilized by passing it through a Gelman 0.2 μm filter.

Analytical Methods

Lactose and ethanol were determined by liquid chromatography using a 6 mm×60 cm column packed with Aminex 50 W-X[4] at 85° C. (Ladisch and Tsao, 1978). Cell density was determined microscopically using a PetroffHausser cell counter.

The Bioreactor

The ICRS consists of two jacketed glass columns packed with either ¼" ceramic Intalox saddles (Norton Co.), a standard gas-liquid contacting packing, or an absorbant matrix. The saddles were coated with 25% gelatin crosslinked by gluteraldehyde (Sitton and Gaddy, 1980; Griffith and Conpere, 1975) to facilitate adsorption of the yeast. A cell suspension was added to the reactor and the cell immobilized by adsorption. FIG. 2 shows a diagram of the complete reactor-separator apparatus.

The enricher with Intalox saddles is 44 mm in diameter and 220 cm tall, with metal plates at 15 cm intervals. The plates have an inner ID of 16 mm. The stripper is a 25 mm ID jacket glass column also 220 cm in height with rubber washers at 15 cm intervals. The enricher and stripper of the absorbant matrix column were initially 44 mm ID but were reduced to 25 mm ID due to the high reaction rates.

Reactor Modeling

As described hereinabove, there is presented a stagewise mathematical model of the ICRS system. (See also Dale et al, 1982). This model incorporated an adsorbed cell surface renewal term with the specific reaction rate per surface area being given as:

$$\hat{r} = X_{so}\gamma \max \exp(-K_p P) \left[\frac{S}{K_g + S}\right] \left[\frac{R}{R + Kd}\right]$$

where $X_{so}$ is the initial adsorbed cell density, $K_g$ is the Monod lactose saturation constant, $K_p$ is the ethanol inhibition constant (Aiba, et al, 1968), R is the surface renewal rate (cm²/cm² hr) and Kd is the death rate constant as defined:

$$X_{s1} = X_{s1} \exp(-Kd\tau)$$

The model demonstrated that satisfactory operation of the ICRS could be obtained at any operating pressure but that the recycle gas mass flow required to obtain a 95% complete separation in the stripper increase linearly from little or no gas at 50 mm to 8 gm $CO_2$/gm $H_2O$ at atmospheric pressure for a feed lactose concentration of 80 gm/Kg. However, the actual volumetric gas flow required for separation remained almost constant as the pressure varied. Therefore, the system must be designed to accommodate a high volumetric gas rate at any operating pressure. This led to the decision to operate the absorbant column at atmospheric pressure.

Results

I. Intalox saddle packed column
A. Axial mixing in the bubble column.

The original apparatus consisted of two 80 mm ID columns one meter in length. At atmospheric pressure with no additional gas flow, a conventional lactose and ethanol profile over the length of the reactor was obtained, but at 50 mm the concentration profiles were constant. It was obvious that at 50 mm Hg the reactor was behaving as two CSTR's in series rather than as a tubular reactor. The axial dispersion coefficient was then determined by injecting a sample under non-flow conditions (Deckwer, et al., (1974) found that the non-flow technique gave values for Dax statistically identical to flow techniques for tall bubble columns).

Figure 8:
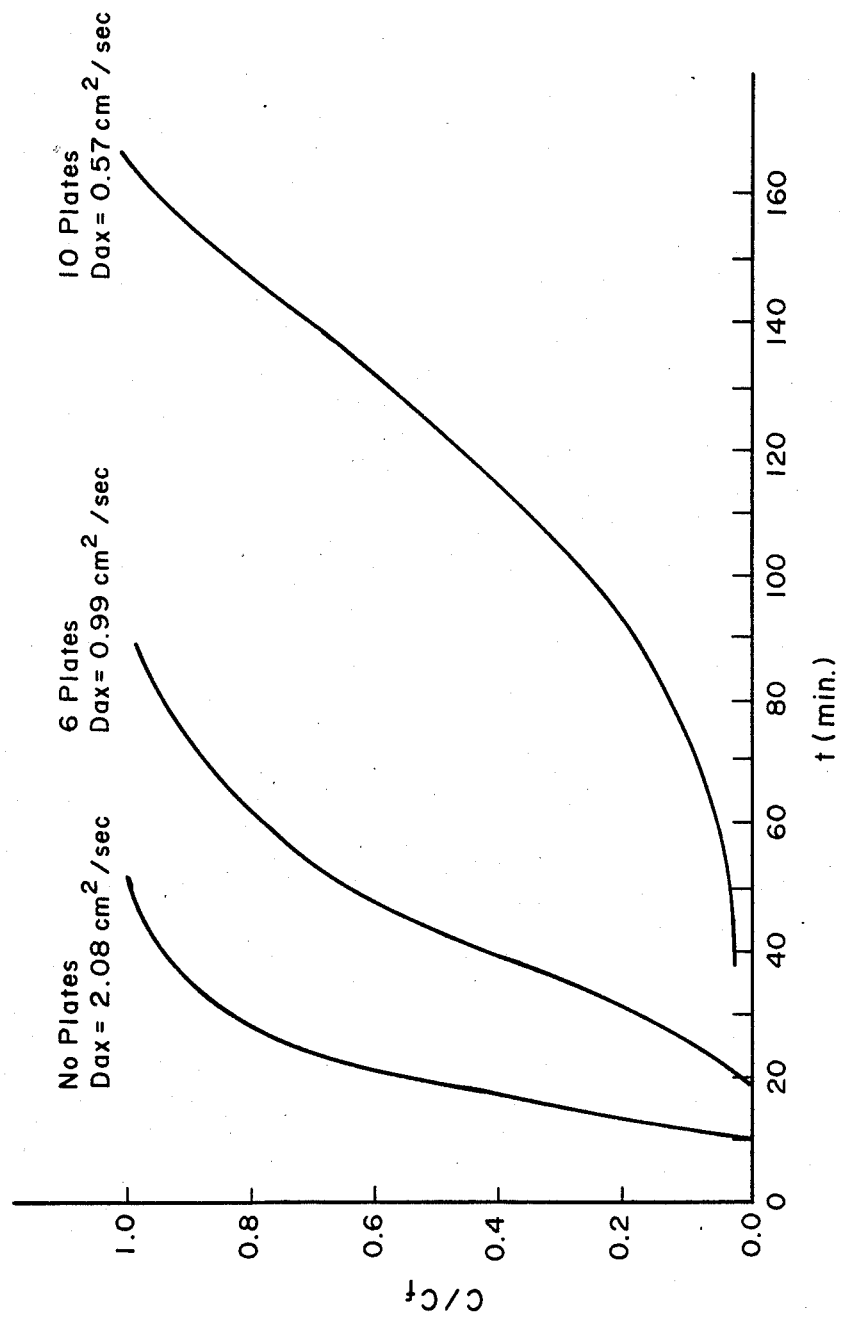
FIG. 8 shows tracer concentration as a function of time—120 cm from injection point.

Axial dispersion in bubble columns is related to gas flow rates and column diameter (Shah, 1980) and can be reduced by column intervals (Magnussen and Schumacher, 1978). Thus, we reduced the column diameter and put baffles or plates at regular intervals. FIG. 8 shows the C/Cf curves determined for the 44 mm ID column with and without plates. The axial dispersion coefficient was determined from these curves by fitting the relatively straight line portion of the C/Cf vs time curve to the analytical solution of the diffusion equation (Ohki and Inoe, 1970). The values of Dax for the various configurations is given in Table 2.

TABLE 2

| Column | Gas Flow Rate (1/m² hr.) | Dax/cm²/s |
|---|---|---|
| 80 mm ID - no plates | 4.8 × 10³ | 3.47 |
| 80 mm ID - 6 plates | 4.8 × 10³ | 1.45 |
| 44 mm ID - no plates | 7.9 × 10³ | 2.08 |
| 44 mm ID - 6 plates | 7.9 × 10³ | 0.98 |
| 44 mm ID - 10 plates | 7.9 × 10³ | 0.56 |

These values agree fairly closely with those reported by Magnusnen and Schumacher (1978) for packed bubble columns and 3.7 cm²/sec. for 10 mm Raschig rings in an 80 mm ID column).

The 44 mm ID column plates were simply steel washers coated with silicone rubber to prevent rusting. The inner diameter of the washer was 18 mm which corresponds to 16.7% free area. Using the value of 0.56 cm²/sec. for Dax in the 44 mm ID column with a reactor length of 220 cm, we can solve for the required liquid velocity to give a Pe value of 12 (corresponding to about 7 CSTR's in series) giving 0.030 cm/s or a residence time of 120 minutes. A 4 hour residence time gives a Pe value of 6.8 (4.5 CSTRS in series).

The composition profile of the 44 mm column with plates showed little indication of serious backmixing even under vacuum conditions. The gas velocity and consequent bubbling turbulence increases dramatically over the length of the enricher due to the combined effects of gas generation by reaction and decreasing pressure. Thus the degree of axial mixing increases with column height. This is typical of most bubble columns but is accentuated by the gas evolution during ethanol fermentation.

B. ICRS Performance—with Intalox Saddles

Liquid Continuous Enricher and Gas Continuous Stripper)

Figure 9:
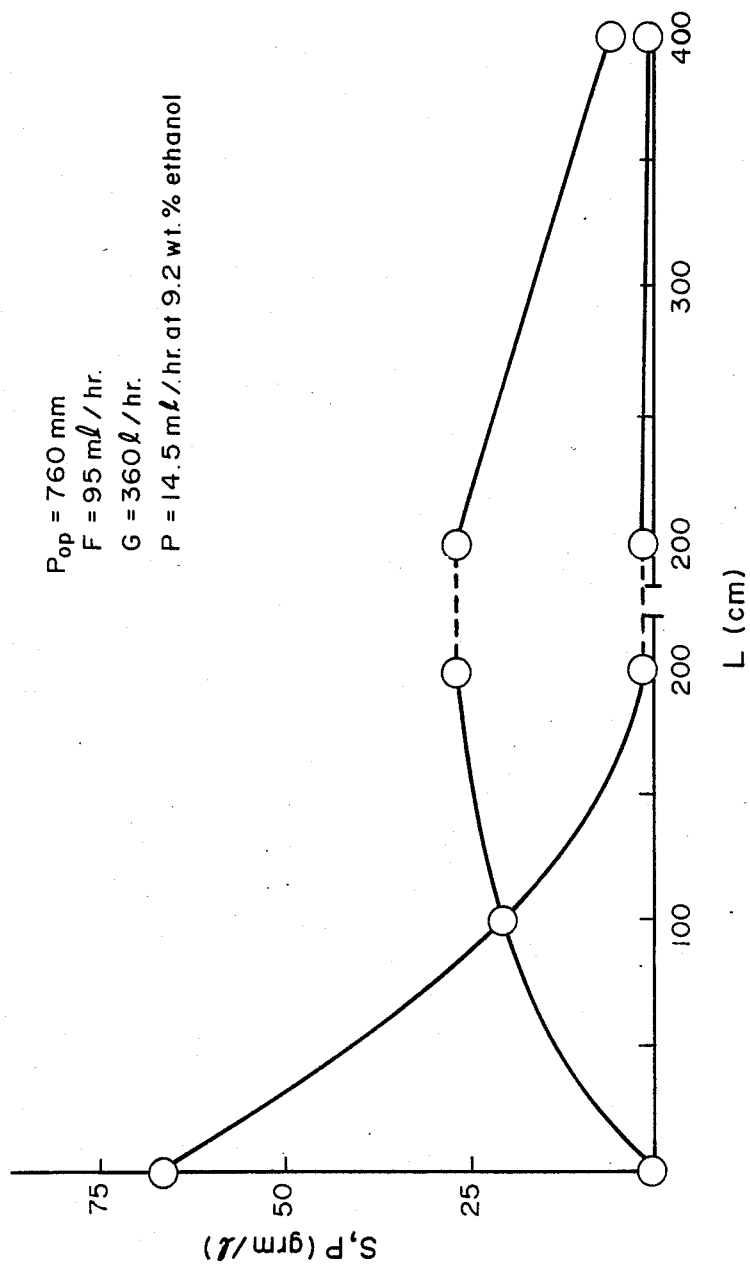
FIG. 9 shows concentration profiles of lactose and ethanol in the reactor-separator.
Figure 10:
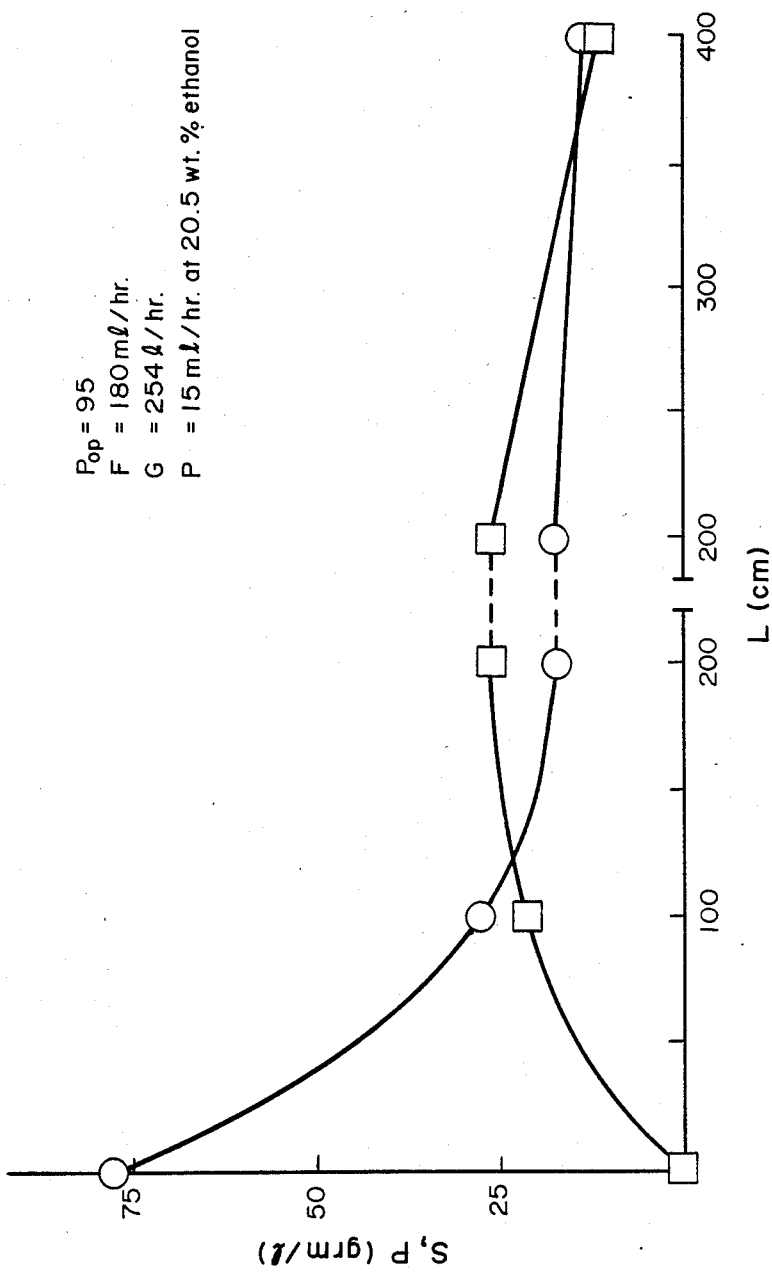
FIG. 10 shows concentration profiles of lactose and ethanol in the reactor-separator, at reduced pressure.
Figure 11:
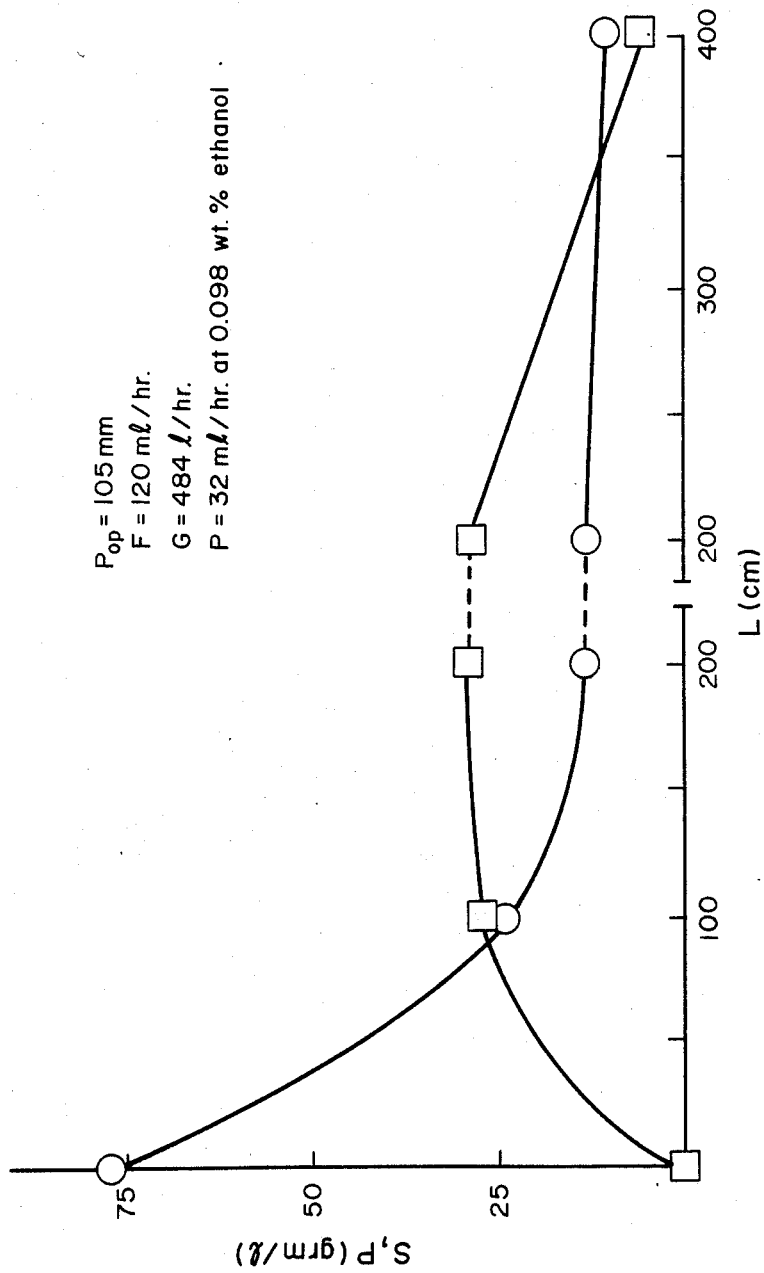
FIG. 11 shows concentration profiles of lactose and ethanol in the reactor-separator, at reduced pressure.

The liquid phase ethanol and lactose composition as a function of ICRS position at 760, 105 and 95 mm are shown in FIGS. 9, 10, and 11. Yeast requires oxygen even under "anaerobic" conditions in order to sustain growth and productivity. Cysewski and Wilke (1976) show that there is an optimal oxygen tension of about 0.7 mm Hg under atmospheric conditions for "anaerobic" fermentation with fermentor cell mass productivity dropping sharply at true anaerobic conditions. The runs shown in FIGS. 9, 10, 11 oxygen was sparged into the bottom of the enricher at a rate of 12 ml/min (atmospheric pressure). In FIG. 9 at 760 mm Hg, we see a fairly complete reaction in the enricher with little or no separation, followed by 72% by the ethanol being separated in the stripper while the residual lactose declined from 2.6 gm/l to 1.1 gm/l. Thus, at atmospheric pressure with no gas introduced into the enricher, the bulk of the reaction took place in the enricher, and most of the separation in the stripper. At 105 mm Hg (FIG. 10), the ICRS profiles were similar to 760 mm Hg but some ethanol was separated in the enricher (10.2% of the ethanol formed was removed in the enricher as determined by mass balance). In the stripping column at a gas flow of 484 l/hr, 72% of the ethanol entering the stripper was stripped while the lactose concentration dropped only from 14.5 to 13.5 gm/l. Decreasing the gas flow rate in the stripper to 254 l/hr (FIG. 11) at 95 mm gave a higher ethanol concentration in the condenser (20.5 wt% as compared to 9.8%) but less complete ethanol removal (48% of the ethanol stripped). Thus we see that the stripping section is providing very little reaction and not performing too well as a stripper either. This is thought to be due to incomplete packing wetting and liquid channeling. The superficial liquid velocity is only 0.016 cm/sec. Dankwerts (1967) shows the wetted area fraction of ½" ceramic Intalox saddles increasing roughly linearly from 0 at no liquid flow to 0.34 at 0.2 cm/sec. If we extrapolate these results to our system only 3% wetting would be expected.

II. ICRS Performance with Adsorbant Matrix Packing

A. Axial Dispersion and Liquid Holdup in a 25 mm ID Column

Figure 12:
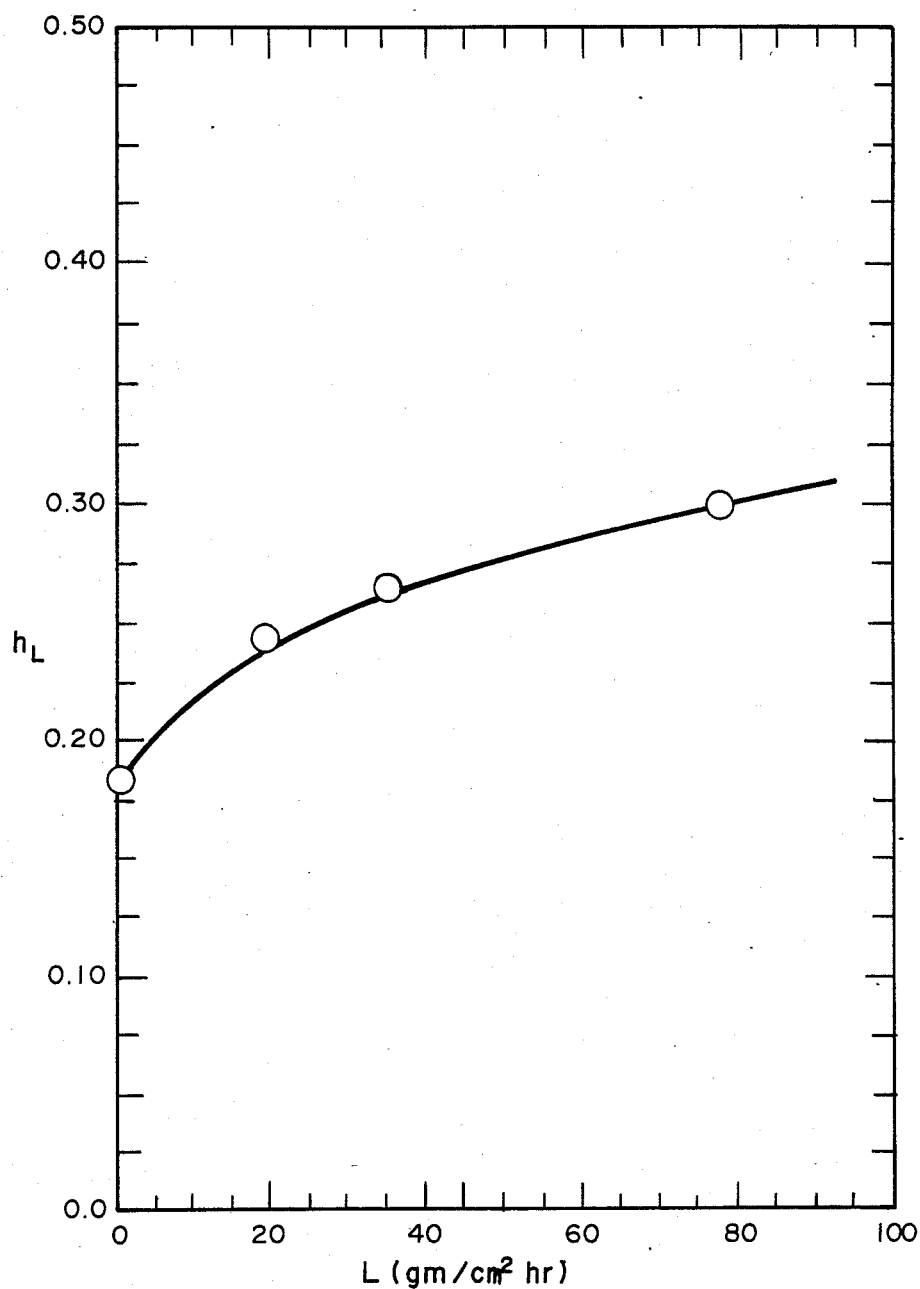
FIG. 12 shows liquid holdup in a 25 mm absorbent matrix column as a function of liquid loading rate.

A 45 cm long 25 mm ID glass column was packed with absorbent packing with a dry weight of 5.51 g. The liquid holdup of the column as a function of liquid loading rate was determined by weighing the column after a steady feed had been established for 2 to 3 hours. The total liquid holdup as a function of liquid loading rate, L, is shown in FIG. 12. There is a slight increase in $h_L$ from 0.19 at L=0 (allowed to drain for 30 minutes) to 0.30 at L=78.2 g/cm$^2$-hr. Thus the liquid holdup is only a slight function of liquid flow rate, and a high liquid holdup is attained at all flows.

Figure 13:
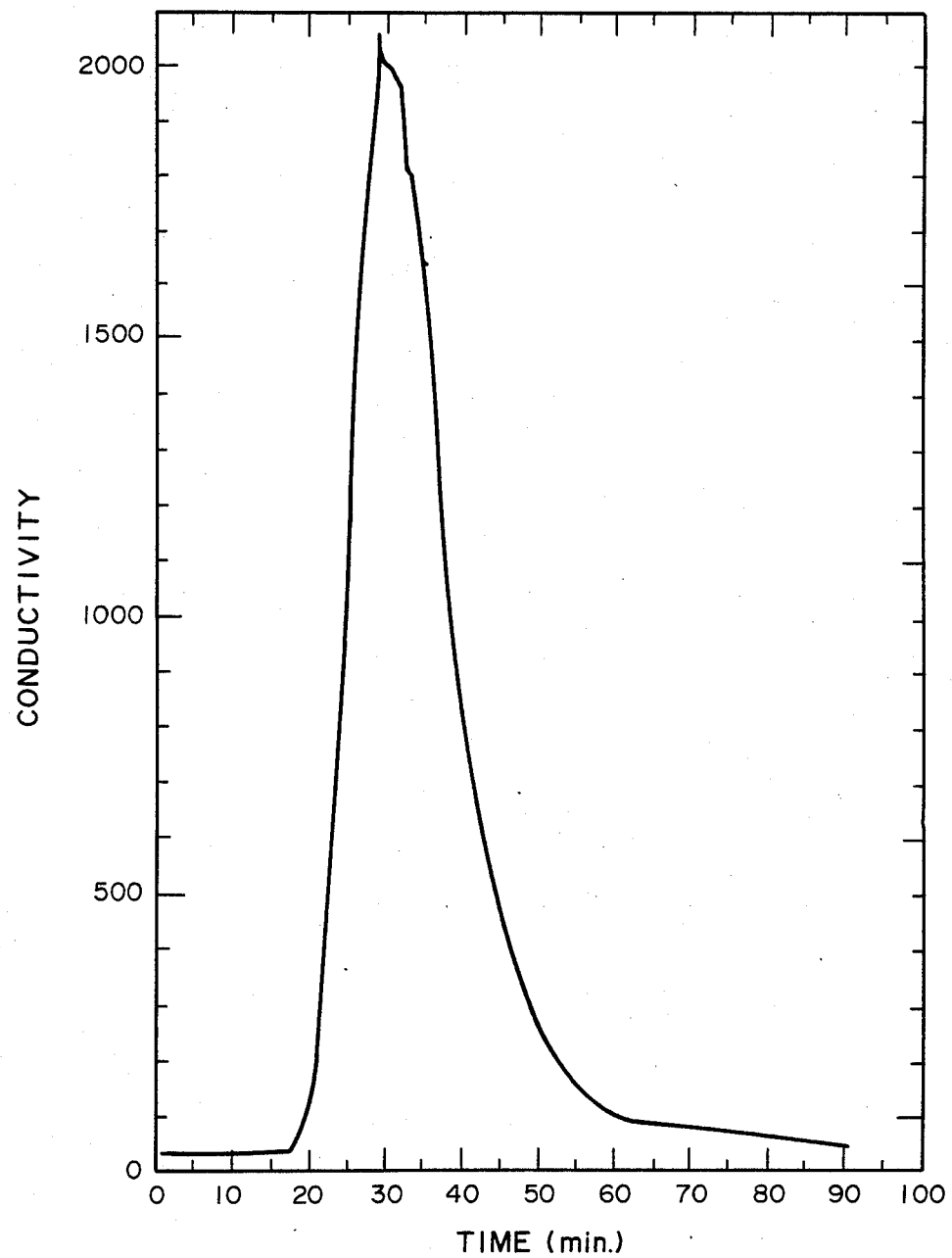
FIG. 13 shows residency time distribution of 25 mm internal diameter absorbent matrix packed column.

The RTD curve at a feed rate of 102 ml/hr is shown in FIG. 13. The average residence time is 36 minutes corresponding to a dynamic liquid holdup of 64 ml or $h_L=0.29$. This was a slightly higher value than determined by weighing the column. The Peclet number determined from the RTD curve is 16.5, giving $D_{ax}$ of 0.016 cm$^2$/s.

B. Separation Efficiency of 25 mm Absorbent packing Column

Figure 14:
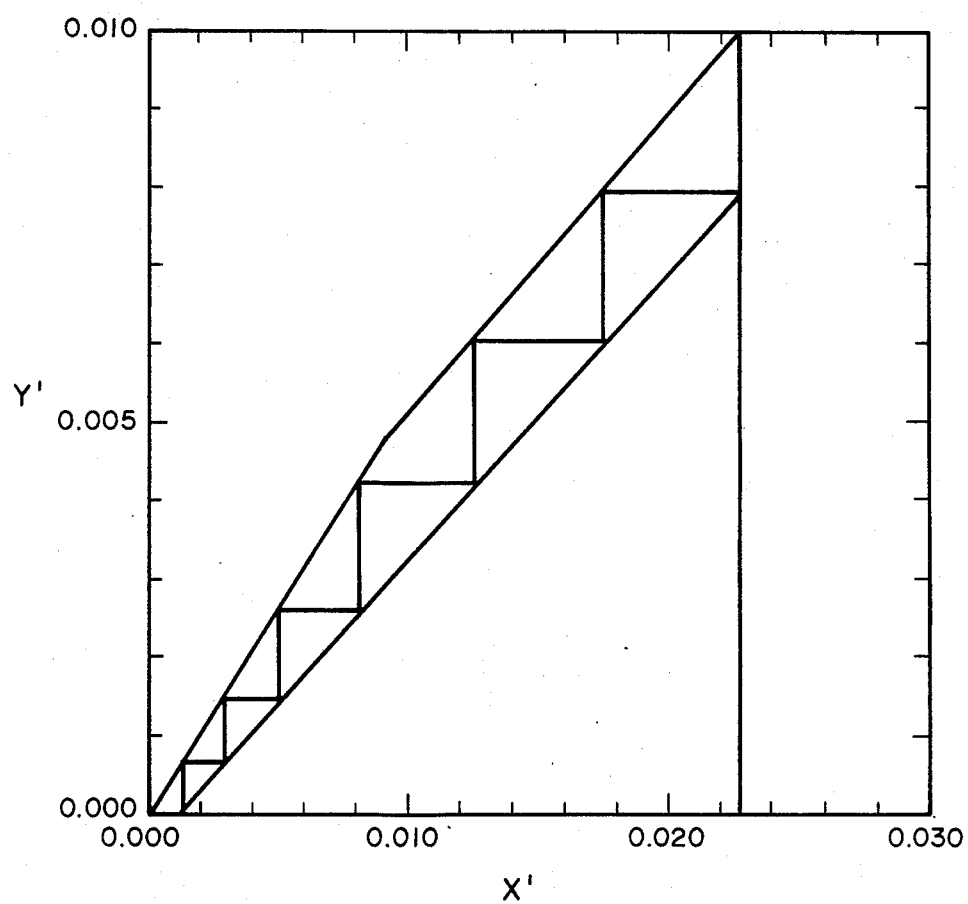
FIG. 14 shows separation efficiency of an 80 cm, 25 mm internal diameter absorbent matrix packed column.

The separation efficiency of an 80 cm by 25 mm ID absorbent packing column was tested using a 5% ethanol solution. The feed was stripped by humid air passing counter-currently up the column. The inlet and outlet liquid phase ethanol concentrations were monitored at various gas flow rates. This data was then plotted on McCable-Theile type plots based on mole ratio ethanol in the gas and liquid phases as shown in FIG. 14. The minimum gas-liquid mole ratio to give a desired separation can be determined based on an infinitely long column. For example, to reduce a 5% ethanol solution to 0.20% ethanol outlet in a stripper gives a minimum $CO_2/H_2O$ ratio of 1.98. In practice values of 1.5 to 3.0 times this minimum is generally used. To use the McCabe-Thiele diagram, the inlet ethanol gas concentration is known to be 0.0, and the gas/liquid molar flow ratio, $G_{st}$ is also known. The operating line may be plotted on this basis and the equilibrium line also plotted. The number of equilibrium stages can then be calculated with the example shown in FIG. 14, giving 6.5 stages. The number of stages was found to vary between 5.0 and 7.5 at various gas flow rates. This gives the height of a theoretical stage (HETP) as 10 to 16 cm. This value is quite good considering the low liquid loading rates (18 g/cm$^2$-hr). The absorbent packing is providing good gas liquid contact and performing well as a column internal. The HETP for absorbent packing is about the same as the value determined for ¼" Intalox saddles by Eckert (1969) of 13 cm for columns run in the 'normal' high liquid loading regimes. Thus the high mass transfer surface area provided by the absorbent packing makes up for the lack of turbulent gas-liquid contact provide by commercial packings run in the normal operating regimes.

C. 25 mm ID ICRS Results

The 25 mm ID ICRS consisted of a 45 cm enricher and 80 cm stripper. The columns were filled with 24 hour cell broth ($3.6 \times 10^8$ cell/ml) and allowed to stand for 4 hours. Then the feed was started to the bottom of the reactor and the columns run liquid continuous for 24 hours before being drained and run gas continuous. The column was run at atmospheric pressure in these runs. Table 3 gives a summary of the ICRS operating parameters and results. The reactor was started out with a feed concentration of 109 g/l. The first data was taken after allowing the reactor to stabilize for 3 days. From the data of table 3, at a feed flow rate of 60 ml/hr, a residency time of 2.6 hour is obtained, while at a feed flow rate of 390 ml/hr, a residency time of 0.4 hour is obtained;

TABLE 3

25 mm ID Absorbent Column ICRS Performance
45 cm Enricher $H_{dL}$ = 64 ml
80 cm Stripper $h_{dL}$ = 95 ml

Figure 15:
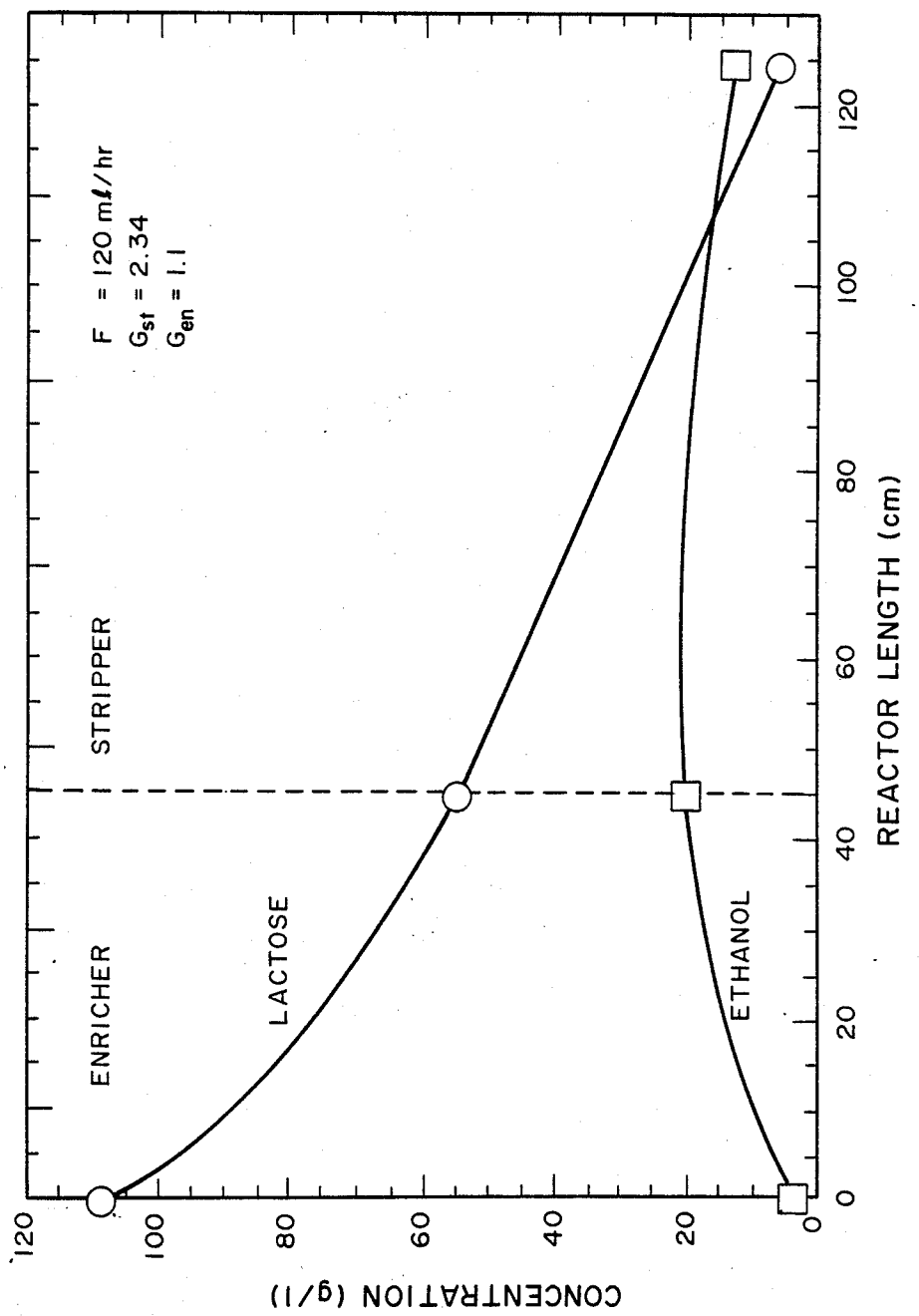
FIG. 15 shows concentration profiles of 25 mm internal diameter absorbent matrix reactor-separator.

| Q(ml/hr) | Enricher | | | | | Stripper | | | |
|---|---|---|---|---|---|---|---|---|---|
| | $S_i$ | $S_o$ | $P_o$ | $G_e$ | $v_{en}$ | $S_o$ | $P_o$ | $G_{st}$ | $v_{s+r}$ |
| 60 | 109 | 1.0 | 37.5 | 1.8 | 50.6 | 1.0 | 4.8 | 3.82 | — |
| 120 | 109 | 54.9 | 20.6 | 1.1 | 50.6 | 6.02 | 14.5 | 2.34 | 32.6 |
| 90 | 215 | 90.9 | 45.7 | 1.7 | 97.8 | 63.4 | 4.6 | 3.4 | 12.9 |
| 62 | 215 | 57.9 | 50.8 | 2.5 | 78.5 | 20.0 | 7.2 | 4.9 | 12.2 |
| 57 | 215 | 55.1 | 44.3 | 2.7 | 73.5 | 0.7 | 2.2 | 5.2 | 16.4 |
| 57 | 215 | 71.6 | 59.8 | 0 | 65.9 | 57.0 | 73.1 | 0 | 4.3 |
| 160 | 57.5 | 1.0 | 23.2 | 0.8 | 72.9 | 1.0 | 6.0 | 1.3 | — |
| 390 | 57.5 | 5.9 | 23.2 | 0.3 | 162.3 | 1.5 | 13.3 | 0.6 | 8.7 | with 109 g/l lactose fed at a rate of 60 ml/hr, the lactose was consumed almost entirely in the enricher. The stripper was efficient, reducing the outlet ethanol level to 4.8 g/l, but as no lactose was fed to the stripper there was no ethanol produced. Doubling the feed rate to 120 ml/hr and waiting 36 hours allowed an outlet lactose concentration of 55 g/l from the enricher to be fed to the stripper. In this case, the stripper reduced the lactose level to 6 g/l and stripped the outlet ethanol to 14.5 g/l. This concentration profile is shown in FIG. 15. The reduction in stripping efficiency due to a lower gas/liquid ratio ($G_{st}$) in the stripper.

The concentration of the lactose in the feed was then raised to test the ability of the ICRS to ferment higher levels of lactose. The feed concentration was raised to 215 g/l lactose at a feed rate of 90 ml/hr. After 24 hours a high productivity was obtained in the enricher (97 g/l-hr), but the stripper only reduced the concentration from 91 to 63 g/l lactose with a productivity of 12.9 g/l-hr. Reducing the feed rate to 62 ml/hr allowed more complete fermentation although the enricher productivity dropped slightly (74 g/l-hr) due to the higher ethanol levels. The reactor was then allowed to run for another 48 hours at the same feed rates (dropped slightly to 57 ml/hr). The lactose utilization improved with the outlet lactose concentration dropping to 2 g/l while the stripper productivity increased to 16.4 g/l-hr. The stripping section worked well at $G_{st}$ of 5.2, reducing the outlet ethanol level to 2.2 g/l. Thus, the ICRS worked well, both reacting and separating. The total effluent lactose was reduced from 21% to less than 0.1% and the ethanol was effectively stripped, giving an outlet stream with about 0.2% ethanol. The condenser ethanol concentration was 27% (w/w). The improvement over time suggests adaptation to the high lactose levels, and is largely due to increases in the productivity of the stripper.

Figure 16:
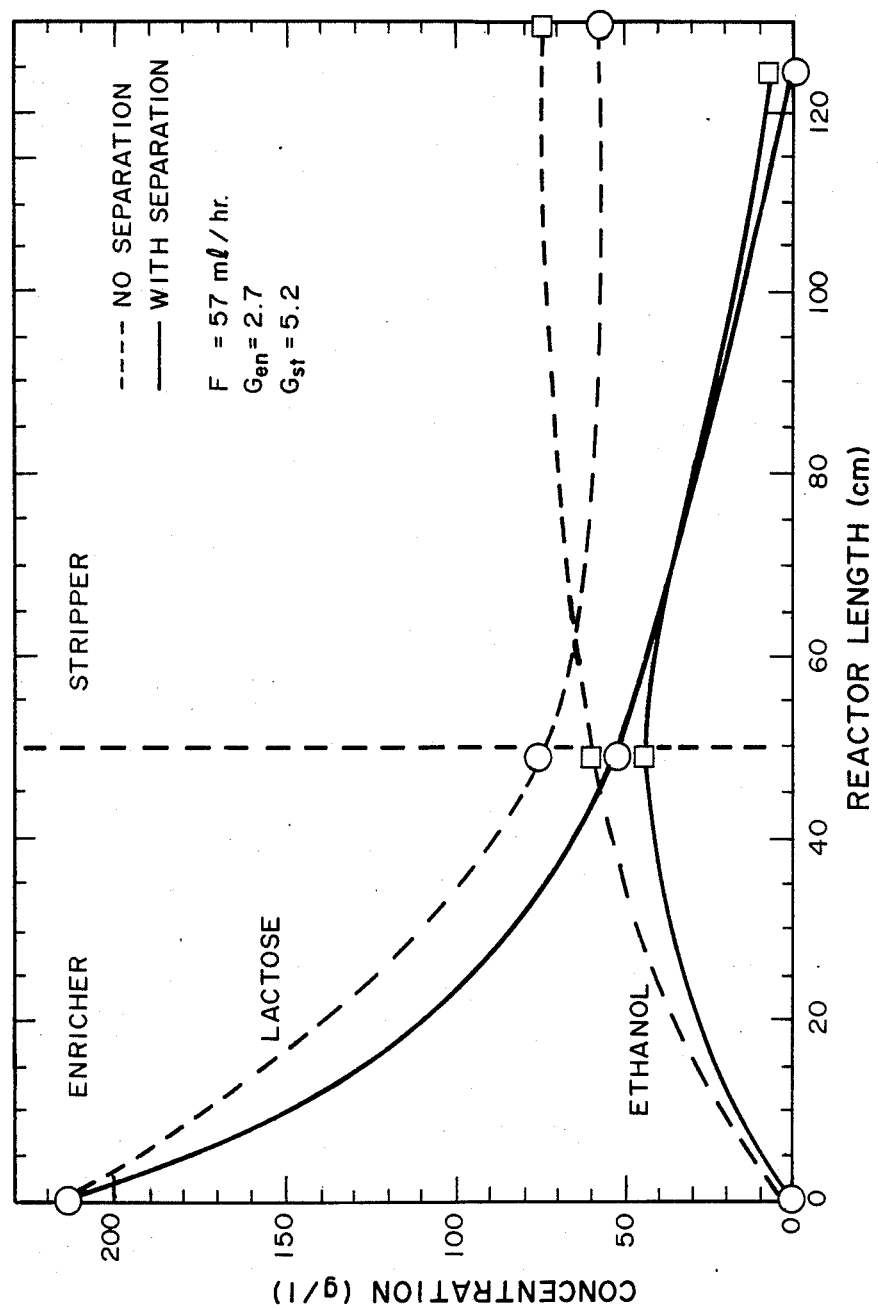
FIG. 16 shows concentration profiles of 25 mm absorbent matrix reactor-separator.

The effect of separation on the ICRS was then determined by shutting off the gas flow through the enricher and stripper. As an ICR the reactor was only able to reduce the lactose level to 5.7% with an outlet ethanol concentration of 7.3%. The productivity of the enricher dropped from 73.5 g/l-hr to 66 g/l-hr, and the stripper productivity dropped much more dramatically from 16.4 to 4.3 g/l-hr, as would be expected due to the presence of high ethanol throughout the stripper. These concentration profiles are shown in FIG. 16.

Figure 17:
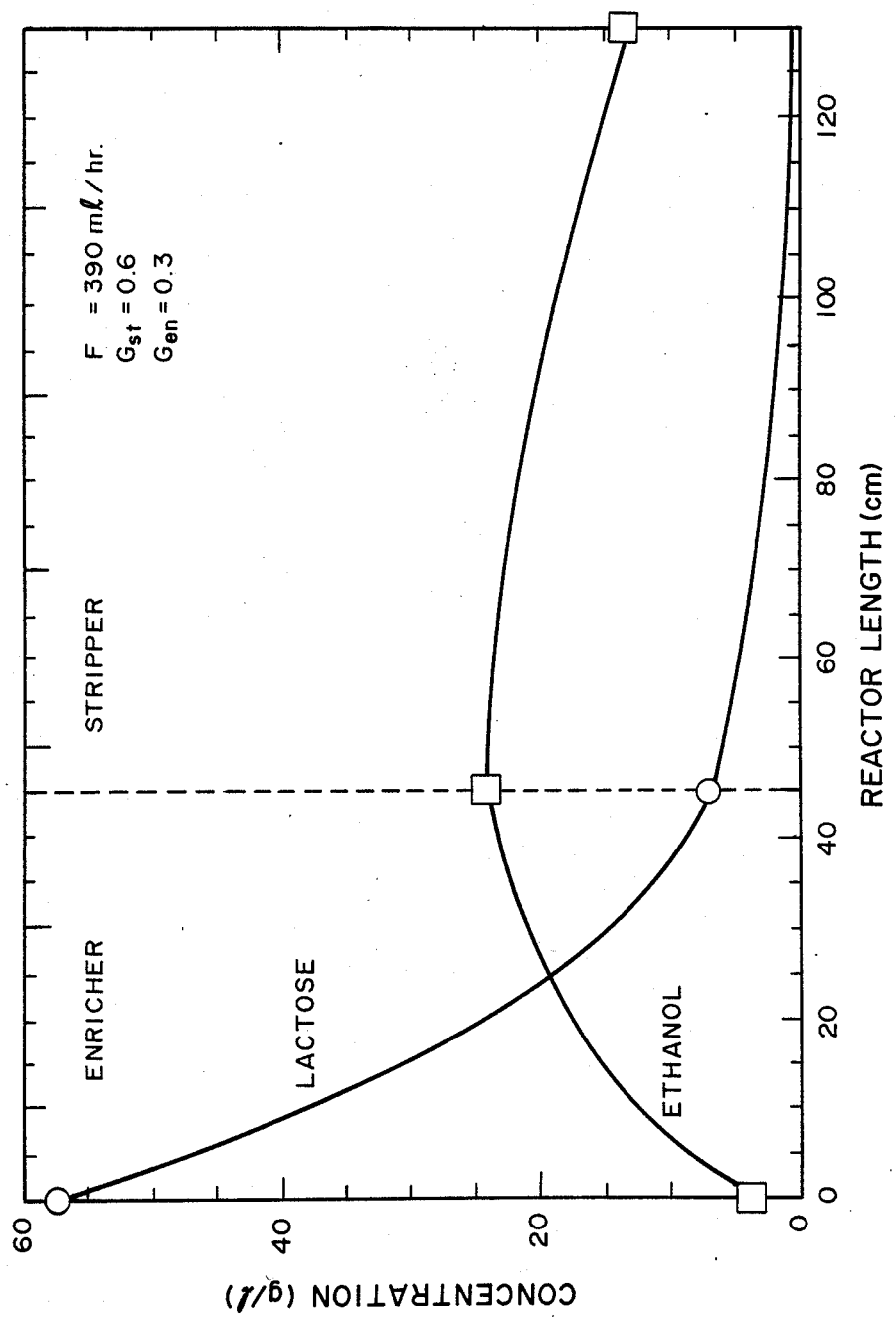
FIG. 17 shows concentration profiles of lactose and ethanol in a 25 mm absorbent matrix reactor-separator.

The lactose feed concentration was reduced to 57 g/l to emulate single strength whey feed. At a flow rate of 160 ml/hr the lactose was completely consumed in the enricher. This corresponds to total lactose utilization in a residence time of about 20 minutes. The feed rate was increased to 390 ml/hr and again almost all the lactose was consumed in the enricher with an outlet lactose concentration of 6 g/l. The concentration profile at a feed rate of 390 ml/hr is shown in FIG. 17. The enricher ethanol productivity was 162 g/l-hr, an extremely high productivity at an average residence time of slightly less than 10 minutes. The stripper reduced the lactose level to 1.5 g/l but only reduced the ethanol level to 13.3 g/l. This was due to the low gas-liquid flow ratio in the stripper. The high liquid flow rates require high gas flows to strip the ethanol. Unfortunately, at a feed flow of 390 ml/hr there was stripper flooding at a gas flow rate of 12 l/min, a $G_{st}$ ratio of only 0.6. The gas pump used in this work was only capable of pumping 20 l/min which would raise the gas/liquid ratio to only around 1.0, while a gas ratio of 4.0 to 5.0 is required to remove 95% of the ethanol.

The absorbent packing column worked well as shown for a period of almost three weeks before it was shut down to determine the adsorbed cell density. Care was taken throughout this period of time to make sure that the feed was never interrupted as an earlier run had shown the yeast died quickly when the feed was shut off.

The gas continuous absorbant packing packed column was found to be fairly resistant to take over by bacteria. Leaking filters allowed the feed tank to become infected with bacteria during these runs, but even though a small concentration of bacteria were actually being fed to the column in the feed, the ICRS continued working well. This resistance to takeover contrasts rremarkably with the liquid continuous system in which the reactor is quickly and totally taken over once bacterial growth starts.

The cell density was determined by emptying the absorbant packing from the column and rinsing it thoroughly. An accurate cell count could not be made due to the presence of large numbers of yeast clumps. These clumps were estimated to have 15-150 cells/clump. Therefore a dry weight was made of the cells removed from the enricher. It was found that approximately 18.5 grams of cells had attached to the absorbant packing. The dry weight of the absorbant packing was 5.51 g, so that the dry weight of the cells was more than 3 times the weight of the absorbant packing support. This corresponds to about $6 \times 10^9$ cell per ml in the enricher or a cell dry weight of 94.3 gm/l per liter reactor. The number of cells in the stripper was determined by running the column in the liquid continuous mode and running high rates of gas through the column to cause a high degree of turbulence in the reactor. Again, a large number of yeast clumps was noted, but it was attempted to determine the number of cells in clumps as compared to the unclumped cells. A ratio of about 1 clumped cell to 2 unclumped cell was estimated. A total cell count of $5.9 \times 10^{11}$ cell was desorbed corresponding to about $1.5 \times 10^9$ cell per ml in the column. This corresponds to a dry cell weight of 7.5 grams or 19.2 gm/l. Thus the cell density in the enricher was about 4 times higher than the stripper, reflecting the better growth conditions. The higher cell concentration was particularly noticeable near the top of the enricher with the packing totally coated with a visible layer of whitish colored yeasts. Given time, the stripper cell density might approach the same cell density as the enricher. However, we would expect higher productivity and better growth conditions in the enricher as the stripper should be run so that there is a high level of ethanol at the top and a low lactose level at the bottom giving slow yeast growth in both regions.

We claim:

1. A method of preparing a volatile fermentation product from a non-volatile fermentable substrate, comprising:
  A. immobilizing cells on a gas porous, absorbent, inert solid matrix supported in a reactor-separator comprising a first fermenter enriching section and a second fermenter stripping section;
  B. continuously introducing a feed solution comprising liquid fermentable substrate and a first stripping gas into the first fermenter section wherein said fermentable substrate and said first stripping gas flow co-currently;
  C. contacting said immobilized cells in the first fermenter section with fermentable substrate wherein at least a part of said fermentable substrate is converted to volatile product and at least a part of said volatile product is stripped by the first stripping gas;
  D. introducing liquid effluent broth comprising fermentable substrate and volatile product from the first fermenter section into the second fermenter section wherein the broth moves countercurrent to a second stripping gas introduced into the second fermenter in a gas continuous environment;
  E. contacting immobilized cells in the second fermenter section with the liquid effluent broth comprising fermentable substrate and volatile product wherein said fermentable substrate is converted into volatile product, and wherein said volatile product enters the gas phase;

F. recovering volatile fermentation product from gases exiting said first and second fermenter sections, wherein the concentration of volatile product and fermentable substrate each comprises less than 20 grams/liter of liquid effluent broth from the second fermenter section;

wherein the combined residence time in both the first fermenter enriching section and second fermenter stripping section is between from 0.4 to 2.6 hours.

2. A method of claim 1 wherein said first and second fermenter sections are operated continuously after initial immobilization of cells onto the absorbent matrix, said feed solution comprising substrate at concentrations ranging from 57 to 215 grams per liter, said second fermenter stripping section being operated with a molar ratio of stripping gas to liquid of between 0 and 5.2 wherein further addition of cells is not required during operation of the fermenter sections.

3. A method of claim 1 wherein the immobilized cells comprise yeast cells.

4. A method of claim 1 wherein the volatile product comprises ethanol.

5. A method of claim 1 wherein the matrix comprises natural sponge.

6. A method of claim 1 wherein the stripping gas comprises carbon dioxide.

7. A method of claim 1 wherein the fermentable substrate comprises lactose.

8. A method of claim 7 wherein the cells comprise yeast cells.

* * * * *